United States Patent
Pimentel et al.

(10) Patent No.: US 9,845,511 B2
(45) Date of Patent: Dec. 19, 2017

(54) METHODS OF DIAGNOSIS, SELECTION, AND TREATMENT OF DISEASES AND CONDITIONS CAUSED BY OR ASSOCIATED WITH METHANOGENS

(71) Applicant: Cedars-Sinai Medical Center, Los Angeles, CA (US)

(72) Inventors: Mark Pimentel, Los Angeles, CA (US); Ruchi Mathur, Los Angeles, CA (US); Christopher Chang, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 15/043,223

(22) Filed: Feb. 12, 2016

(65) Prior Publication Data
US 2016/0244813 A1    Aug. 25, 2016

Related U.S. Application Data

(62) Division of application No. 14/211,197, filed on Mar. 14, 2014, now Pat. No. 9,289,418.

(60) Provisional application No. 61/792,687, filed on Mar. 15, 2013.

(51) Int. Cl.

| | | |
|---|---|---|
| *A61K 31/4164* | (2006.01) | |
| *C12Q 1/68* | (2006.01) | |
| *A61K 31/155* | (2006.01) | |
| *A61K 31/437* | (2006.01) | |
| *A61K 35/741* | (2015.01) | |
| *A61K 45/06* | (2006.01) | |
| *A61K 31/137* | (2006.01) | |
| *A61K 31/22* | (2006.01) | |
| *A61K 31/366* | (2006.01) | |
| *A61K 31/40* | (2006.01) | |
| *A61K 31/404* | (2006.01) | |
| *A61K 31/454* | (2006.01) | |
| *A61K 31/47* | (2006.01) | |
| *A61K 31/505* | (2006.01) | |
| *A61K 31/7036* | (2006.01) | |
| *A61K 31/7048* | (2006.01) | |
| *A61K 31/337* | (2006.01) | |
| *A61K 31/351* | (2006.01) | |
| *A61K 31/357* | (2006.01) | |
| *A61K 31/55* | (2006.01) | |

(52) U.S. Cl.
CPC ............ *C12Q 1/689* (2013.01); *A61K 31/137* (2013.01); *A61K 31/155* (2013.01); *A61K 31/22* (2013.01); *A61K 31/337* (2013.01); *A61K 31/351* (2013.01); *A61K 31/357* (2013.01); *A61K 31/366* (2013.01); *A61K 31/40* (2013.01); *A61K 31/404* (2013.01); *A61K 31/4164* (2013.01); *A61K 31/437* (2013.01); *A61K 31/454* (2013.01); *A61K 31/47* (2013.01); *A61K 31/505* (2013.01); *A61K 31/55* (2013.01); *A61K 31/7036* (2013.01); *A61K 31/7048* (2013.01); *A61K 35/741* (2013.01); *A61K 45/06* (2013.01); *C12Q 2600/106* (2013.01)

(58) Field of Classification Search
CPC .................................................. C12Q 2600/106
See application file for complete search history.

(56) References Cited

U.S. PATENT DOCUMENTS

| | | | |
|---|---|---|---|
| 5,232,946 | A | 8/1993 | Hurnaus et al. |
| 5,447,850 | A | 9/1995 | McCann |
| 5,840,332 | A | 11/1998 | Lerner et al. |
| 5,889,038 | A | 3/1999 | Lencer et al. |
| 5,977,175 | A | 11/1999 | Lin |
| 5,985,907 | A | 11/1999 | Wolin et al. |
| 6,036,950 | A | 3/2000 | Baker |
| 6,201,014 | B1 | 3/2001 | Gardiner |
| 6,299,774 | B1 | 10/2001 | Ainsworth et al. |
| 6,328,959 | B1 | 12/2001 | Kayar et al. |
| 6,368,591 | B1 | 4/2002 | Chen et al. |
| 6,495,567 | B1 | 12/2002 | Lencer et al. |
| 6,558,708 | B1 | 5/2003 | Lin |
| 6,562,629 | B1 | 5/2003 | Lin et al. |
| 6,805,852 | B2 | 10/2004 | Lin et al. |
| 6,861,053 | B1 | 3/2005 | Lin et al. |
| 7,048,906 | B2 | 5/2006 | Lin et al. |
| 7,056,686 | B2 | 6/2006 | Lin et al. |
| 7,081,239 | B2 | 7/2006 | Lin |

(Continued)

FOREIGN PATENT DOCUMENTS

| | | |
|---|---|---|
| AU | 2002256254 B2 | 1/2007 |
| AU | 2003273141 B2 | 5/2009 |

(Continued)

OTHER PUBLICATIONS

Kang et al. Diabetes Metab J., 2012, 36:13-15.*

(Continued)

*Primary Examiner* — Bin Shen
(74) *Attorney, Agent, or Firm* — Linda B. Huber; Nixon Peabody LLP

(57) ABSTRACT

The invention described herein provides for methods and systems for determining, selecting, and/or treating diseases and conditions caused by or associated with high quantities of methanogens in a subject, or diseases and conditions caused by or associated with low quantities of methanogens in a subject. In various embodiments, a therapy to inhibit the growth of methanogens or to promote the growth of methanogens are selected and/or administered to a subject in need thereof.

23 Claims, 16 Drawing Sheets

(56) References Cited

U.S. PATENT DOCUMENTS

| | | |
|---|---|---|
| 7,244,412 B2 | 7/2007 | Lin |
| 7,452,857 B2 | 11/2008 | Lin et al. |
| 7,585,838 B2 | 9/2009 | Lin et al. |
| 7,605,240 B2 | 10/2009 | Lin et al. |
| 7,608,245 B2 | 10/2009 | Lin |
| 7,615,207 B2 | 11/2009 | Lin |
| 7,718,608 B2 | 5/2010 | Lin et al. |
| 7,736,622 B2 | 6/2010 | Lin et al. |
| 7,935,799 B2 | 5/2011 | Lin et al. |
| 8,110,177 B2 | 2/2012 | Lin et al. |
| 8,197,805 B2 | 6/2012 | Lin et al. |
| 8,388,935 B2 | 3/2013 | Lin et al. |
| 8,562,952 B2 | 10/2013 | Lin |
| 9,066,962 B2 | 6/2015 | Pimentel et al. |
| 9,192,618 B2 | 11/2015 | Pimentel et al. |
| 9,289,418 B2 | 3/2016 | Pimentel et al. |
| 9,358,245 B2 | 6/2016 | Pimentel et al. |
| 9,358,276 B2 | 6/2016 | Lin et al. |
| 2002/0028269 A1 | 3/2002 | Verrips |
| 2002/0039599 A1 | 4/2002 | Lin et al. |
| 2006/0057197 A1 | 3/2006 | Han et al. |
| 2006/0193871 A1 | 8/2006 | Lin |
| 2006/0246045 A1 | 11/2006 | Pimentel et al. |
| 2007/0280949 A1 | 12/2007 | Alfa |
| 2008/0138320 A1 | 6/2008 | Pimentel et al. |
| 2008/0182291 A1 | 7/2008 | Pimentel |
| 2009/0233888 A1 | 9/2009 | Lin |
| 2009/0246177 A1 | 10/2009 | Horn et al. |
| 2010/0048595 A1 | 2/2010 | Gordon et al. |
| 2010/0055173 A1 | 3/2010 | Penhasi et al. |
| 2010/0172874 A1 | 7/2010 | Turnbaugh et al. |
| 2010/0184624 A1* | 7/2010 | Samuel .................. C12Q 1/689 506/17 |
| 2012/0219527 A1 | 8/2012 | Perdok |
| 2014/0206636 A1 | 7/2014 | Lin et al. |
| 2014/0228431 A1 | 8/2014 | Pimentel et al. |
| 2015/0099713 A1 | 4/2015 | Pimentel et al. |
| 2015/0306190 A1 | 10/2015 | Lin et al. |
| 2016/0038562 A1 | 2/2016 | Pimentel et al. |
| 2016/0045604 A1 | 2/2016 | Pimentel et al. |

FOREIGN PATENT DOCUMENTS

| | | |
|---|---|---|
| AU | 2007201246 A1 | 12/2009 |
| CA | 2486585 C | 7/2012 |
| CN | 105208861 A | 12/2015 |
| EP | 1385476 | 2/2004 |
| EP | 1 609 852 A1 | 12/2005 |
| EP | 1200828 B1 | 10/2007 |
| EP | 2261664 A2 | 12/2010 |
| EP | 2267445 A1 | 12/2010 |
| EP | 1505989 B1 | 2/2011 |
| EP | 2305213 A2 | 4/2011 |
| EP | 1811303 B1 | 6/2011 |
| EP | 2261665 B1 | 6/2014 |
| EP | 2251017 B1 | 3/2015 |
| EP | 2256498 B1 | 4/2015 |
| EP | 2 967 060 A2 | 1/2016 |
| GB | 423083 A | 1/1935 |
| GB | 2 338 244 A | 12/1999 |
| JP | 60-133852 | 7/1985 |
| JP | 03-275630 | 12/1991 |
| JP | 08-310960 | 11/1996 |
| JP | 2005-526861 | 9/2005 |
| JP | 2009-102401 | 5/2009 |
| JP | 4653936 | 12/2010 |
| JP | 2016-516717 A | 6/2016 |
| WO | 01/11077 A2 | 2/2001 |
| WO | 0132162 A1 | 5/2001 |
| WO | 0134123 A1 | 5/2001 |
| WO | 02/083926 A2 | 10/2002 |
| WO | 03/100023 A2 | 12/2003 |
| WO | 2004021972 A2 | 3/2004 |
| WO | WO 2005/058861 A1 | 6/2005 |
| WO | 2005115380 A2 | 12/2005 |
| WO | WO 2006/102350 A1 | 9/2006 |
| WO | WO 2008/044236 A2 | 4/2008 |
| WO | WO 2010/088633 A2 | 8/2010 |
| WO | 2011103123 A2 | 8/2011 |
| WO | WO 2012/124973 A2 | 9/2012 |
| WO | 2014152754 A2 | 9/2014 |
| WO | 2016025762 A1 | 2/2016 |
| WO | WO 2016/161085 A1 | 10/2016 |

OTHER PUBLICATIONS

Miller et al. J. Dairy Sci., 2001, 84:1445-1448.*
PCT/US2014/027697 International Search Report and Written Opinion dated Oct. 3, 2014; 9 pages.
Basseri et al. Intestinal Methane Production in Obese Individuals Is Associated with a Higher Body Mass Index. Gastroenterology & Hepatology (2012). 8(1): 22-28.
Kim et al. Methanobrevibacter smithi is the Predominant Methanogen in Patients with Constipation-Predominant IBS and Methane on Breath. Dig Dis Sci (2012). 57:3213-3218.
Low et al. A Combination of Rifaximin and Neomycin is Most Effective in Treating Irritable Bowel Syndrome Patients with Methane on Lactulose Breath Test. J Clin Gastroenterol (2010). 44:547-550.
Mathur et al. Intestinal Methanobrevibacter smithii but Not Total Bacteria is Related to Diet-Induced Weight Gain in Rats. Obesity (2013). 21(4): 748-754.
Quigley et al. Small Intestinal Bacterial Overgrowth: Roles of Antibiotics, Prebiotics, and Probiotics. Gastroenterology (2006). 130:S78-S90.
Zhang et al. Human gut microbiota in obesity and after gastric bypass. PNAS (2008). pp. 1-6.
PCT/US2015/045140 International Search Report and Written Opinion dated Nov. 19, 2015; 7 pages.
PCT/US03/16656 International Search Report dated Dec. 18, 2003; 2 pages.
PCT/US03/16656 International Preliminary Examination Report dated Jun. 14, 2004; 4 pages.
PCT/US2016/025214 International Search Report and Written Opinion dated Jun. 2, 2016; 13 pages.
EP 03741819.1 Supplemental Search Report dated Apr. 5, 2007; 4 pages.
EP 10173966.2 Supplemental Search Report dated Sep. 30, 2010; 3 pages.
EP 10173966.2 European Extended Search Report dated Oct. 14, 2010; 8 pages.
EP 14770590.9 Extended Search Report dated Oct. 26, 2016; 11 pages.
Alander M., et al., "The effect of probiotic strains on the microbiota of the Simulator of the Human Intestinal Microbial Ecosystem (SHIME)," Int. J. Food Microbiol. 46(1):71-79 (Jan. 1999).
Bakker-Arkema et al., Safety Profile of Atorvastatin-Treated Patients With Low LDL-Cholesterol Levels, Atherosclerosis, (2000), 149(1): 123-129.
Bentley, D.W., et al., "The microflora of the human ileum and intrabdominal colon: results of direct needle aspiration at surgery and evaluation of the technique," J Lab Clin Med. 79(3):421-9 (Mar. 1972).
Bjorneklett, A., et al., "Bacterial overgrowth in jejunal and ileal disease," Scand J Gastroenterol. 18(2):289-98 (Mar. 1983).
Black et al., An Overview of the Clinical Safety Profile of Atorvastatin (Lipitor), A New HMG-CoA Reductase Inhibitor, Archives of Internal Medicine, (Mar. 23, 1998), 158(6):577-584.
Bond, J.H. Jr., et al., "Investigation of small bowel transit time in man utilizing pulmonary hydrogen (H2) measurements," J Lab Clin Med. 85(4):546-555 (Apr. 1975).
Camilleri, M., et al., "Efficacy and safety of alosetron in women with irritable bowel syndrome: a randomised, placebo-controlled trial," Lancet. 355(9209):1035-40 (Mar. 2000).
Cann, P.A., et al., "Irritable bowel syndrome: relationship of disorders in the transit of a single solid meal to symptom patterns," Gut 24(5):405-11 (May 1983).

(56) References Cited

OTHER PUBLICATIONS

Castiglione, F., et al. "Orocecal transit time and bacterial overgrowth in patients with Crohn's disease," J Clin Gastroenterol. 31(1):63-66 (Jul. 2000).
Chang, C. S., et al., "Increased accuracy of the carbon-14 D-xylose breath test in detecting small-intestinal bacterial overgrowth by correction with the gastric emptying rate," Eur. J. Nucl. Med. 22(10):1118-22 (Oct. 1995).
Charteris W.P., et al., "Antibiotic susceptibility of potentially probiotic Lactobacillus species," J. Food Prot. 61(12):1636-43 (Dec. 1998).
Chatterjee et al. "The degree of breath methane production in IBS correlates with the severity of constipation," Am. J. Gastroenterology 2007; 102: 837-841.
Chaucheryras F, et al., "In vitro $H_2$ utilization by ruminal acetogenic bacterium cultivated alone or in association with an archaea methanogen is stimulated by a probiotic strain of Saccharomyces cerevisiae," Appl Environ Microbiol 61(9):3466-7 (Sep. 1995).
Collins, S.M., et al., "Stress, inflammation and the irritable bowel syndrome," Canadian Journal of Gastroenterology. 13 Suppl:47A-49A (Mar. 1999).
Corazza, G., et al., "Prevalence and consistency of low breath H2 excretion following lactulose ingestion. Possible implications for the clinical use of the H2 breath test," Dig. Dis. Sci. 38(11):2010-16 (Nov. 1993).
De Boissieu, D., et al., "Small-Bowel bacterial overgrowth in children with chronic diarrhea, abdominal pain, or both," J Pediatr. 128(2):203-7 (Feb. 1996).
Dellert, S.F., et al., "The $^{13}$C-xylose breath test for the diagnosis of small bowel bacterial overgrowth in children," J. Pediatr. Gastroenterol. Nutr. 25(2):153-58 (Aug. 1997).
Dobson, C.L. et al., "The effect of oleic acid on the human ileal brake and its implications for small intestinal transit of tablet formulations," Pharm. Res. 16(1):92-96 (Jan. 1999).
Drossman, D. A., et al, "Bowel patterns among subjects not seeking health care. Use of a questionnaire to identify a population with bowel dysfunction," Gastroenterology. 83(3):529-34 (Sep. 1982).
Engels et al., Symptomless Colonisation by Clostridium Difficile and Risk of Diarrhoea, The Lancet, (Jun. 6, 1998), p. 1733, 351:9117, London, Great Britain.
Fass., R., et al., "Evidence and consensus-based practice guidelines for the diagnosis of irritable bowel syndrome," Arch Intern Med. 161(17):2081-88 (Sep. 2001).
Fiedorek, S.C., et al, "Breath methane production in children with constipation and encoparesis," J Pediatr Gastroenterol and Nutrition 10(4):473-77 (May 1990).
Funayama, Y., et al., "Monitoring and antibacterial treatment for postoperative bacterial overgrowth in Crohn's disease," Dis Colon Rectum. 42(8):1072-7 (Aug. 1999).
Galatola, G., et al., "Diagnosis of bacterial contamination of the small intestine using the 1g [14C] xylose breath test in various gastrointestinal diseases," Menerva Gastroenterologic Dietologica 37(3):169-75 (Jul.-Sep. 1991) (Abstract in English).
Gardiner, G., et al., "Development of a probiotic cheddar cheese containing human-derived Lactobacillus paracasei strains," Appl. Environ. Microbiol. 64(6):2192-99 (Jun. 1998).
Ghoshal et al. Irritable bowel syndrome and small intestinal bacterial overgrowth: Meaningful association or unnecessary hype. World J Gastroenterol (2014). 20(10):2482-2491.
Gorbach, S.L., "Intestinal Microflora," Gastroenterology. 60(6):1110-29 (Jun. 1971).
Grundy, D., "Mechanisms for the symptoms of irritable bowel disease-possible role of vagal afferents," In, Neurogastroenterology from the Basics to the Clinics. H-J Drammer and MV Singer, Editors, Klumer Academic Publishers, Boston, 2000, pp. 659-663.
Hoeg et al., Effects of Combination Cholestyramine-Neomycin Treatment on Plasma Lipoprotein Concentrations in Type II Hyperlipoproteinemia, American Journal of Cardiology, May 1, 1985; 55(11):1282-1286.

Hoshino et al., Maldigestion/Malabsorption in the Various Gastrointestinal and Liver Diseases. Results of Breath Hydrogen and Methane Analysis, Digestion & Absorption, (1998), 21(1):55-60.
Hutchinson, R., et al., "Scintigraphic measurement of ieocaecal transit in irritable bowel syndrome and chronic idiopathic constipation," Gut 36(4):585-9 (Apr. 1995).
Hwang et al. Evaluating Breath Methane as a Diagnostic Test for Constipation-Predominant IBS. Dig Dis Sci (2010). 55(2): 398-403.
Joseph, F. Jr., et al, "Breath testing: diseased versus normal patients," J Pediatr Gastroenterol. 7(5):787-8 (Sep.-Oct. 1988).
Kehrer et al. Modulation of Irinotecan-Induced Diarrhea by Cotreatment With Neomycin in Cancer Patients. Clinical Cancer Research, May 2001, 7(1), pp. 1136-1141.
Kerlin, P., et al., "Breath hydrogen testing in bacterial overgrowth of the small intestine," Gastroenterology. 95(4):982-88 (Oct. 1988).
King, C.E., et al., "Breath tests in the diagnosis of small intestinal bacterial overgrowth," Crit. Rev. Lab. Sci. 21(3):269-81 (1984).
King, C.E., et al., "Comparison of the 1-gram [14C]xylose, 10-gram lactulose-H2, and 80 gram glucose-H2 breath tests in patients with small intestine bacterial overgrowth," Gastroenterology 91(6):1447-51 (Dec. 1986).
King, T.S., et al., "Abnormal colonic fermentation in irritable bowel syndrome," Lancet 352(9135):1187-89 (Oct. 1998).
Koide, A., et al., "Quantitative analysis of bowel gas using plain abdominal radiograph in patients with irritable bowel syndrome, " Am J Gastroenterol, 92(7):1735-41 (Jul. 2000).
Kontula, P., et al., "The effect of lactose derivatives on intestinal lactic acid bacteria," J. Dairy Sci. 82(2):24956 (Feb. 1999).
Kruis, W., et al., "A diagnostic score for the irritable bowel syndrome," Gastroenterology. 87(1):1-7 (Jul. 1984).
Kumar, D., et al., "The irritable bowel syndrome: a paroxysmal motor disorder," Lancet. 2(8462):973-77 (Nov. 1985).
Kunkel et al. Methane on Breath Testing is Associated with Constipation: A systematic review and Meta-analysis. Dig Dis Sci (2011). 56(6): 1612-1618.
Lewindon, P.J., et al., "Bowel dysfunction in cystic fibrosis: importance of breath testing," J. Pediatr. Child Health 34(1):79-82 (Feb. 1998).
Lin, H.C. et al., "Intestinal transit is more potently inhibited by fat in the distal (ileal brake) than in the proximal (jejunal brake) gut," Dig. Dis. Sci. 42(1):19-25 (Jan. 1997).
Lin, H.C. et al., "Jejunal brake: inhibition of intestinal transit by fat in the proximal small intestine," Dig. Dis. Sci., 41(2):326-29 (Feb. 1996).
Levitt, M.D., et al., "Hydrogen and methane production in man," Ann NY Acad Sci. 150(1):75-81 (Feb. 1968).
McKay, L.F., et al., "Methane and hydrogen production by human intestinal anaerobic bacteria," Acta Pathol Microbiol Immunol Scand [B]. 90(3):257-60 (Jun. 1982).
McKay, L.F., et al., "Methane excretion in man-a study of breath, flatus and faeces," Gut 26(1):69-74 (Jan. 1983).
Melcher, E.A., et al., "Methane production and bowel function parameters in healthy subjects on low-and high fiber diets," Nutrition and Cancer. 16(2):85-92 (1991).
Naidu, A.S., et al., "Probiotic spectra of lactic acid bacteria," Crit. Rev. Food Sci. Nutr. 38(1):13-126 (Jan. 1999).
Nayak, A., et al., "Metronidazole relieves symptoms in irritable bowel syndrome: the confusion with so-called 'chronic amebiasis'," Indian J Gastroenterol 16(4):137-39 (Oct. 1997).
Neal, K.R., et 1., "Prevalence of gastrointestinal symptoms six months after bacterial gastroenteritis and risk facts for development of the irritable bowel syndrome: postal survey of patients," BMJ 314(7083):779-82 (Mar. 1997).
Nichols, R.L., et al., "Ileal microflora in surgical patients," J Urol 105(3):351-3 (Mar. 1971).
Niedzielin et al. "A controlled, double-blind, randomized study on the efficacy of Lactobacillus plantarum 299V in patients with irritable bowel syndrome," Euro. J. of Gastroenterology & Hepatology: Oct. 2001, vol. 13, Issue 10, pp. 1143-1147.
Nobaek, et al. "Alteration of intestinal microflora is associated with reduction in abdominal bloating and pain in patients with irritable bowel syndrome," Am. J. Gastroenterology (2000) 95, 1231-1238.

(56) References Cited

OTHER PUBLICATIONS

Novick et al. "A randomized, double-blind, placebo-controlled trial of tegaserod in female patients suffering from irritable bowel syndrome with constipation," Aliment. Pharmacol. Ther. 2002; 16: 1877-1888.
Nguyen et al., Diarrhea Caused by Enterotoxigenic Bacteroides Fragilis in Children Less Than 5 Years of Age in Hanoi, Vietnam, Anaerobe, (Feb. 2005), pp. 109-114, 11:1-2, London, Great Britain.
Olesen et al. "Efficacy, safety, and tolerability of fructooligosaccharides in the treatment of irritable bowel syndrome," Am. J. Clin. Nutr. 2000; 72: 1570-1575.
Peled, Y., et al., "Factors affecting methane production in humans. Gastrointestinal diseases and alterations of colonic flora," Dig Dis Scr. 32(3):267-71 (Mar. 1987).
Pimentel et al. "Methane, a gas produced by enteric bacteria, slows intestinal transit and augments small intestinal contractile activity," Am. J. Physiol. Gastrointest. Liver Physiol. 2006; 290: G1089-G1095.
Pimentel et al. "Neomycin improves constipation-predominant irritable bowel syndrome in a fashion that is dependent on the presence of methane gas: Subanalysis of a double-blind randomized controlled study," Dig. Dis. Science 2006; 51: 1297-1301.
Pimentel, M., et al., "Eradication of small intestinal bacterial overgrowth reduces symptoms of irritable bowel syndrome," Am J Gastroenterol. 95(12):3503-6 (Dec. 2000).
Plaut, A.G., et al, "Studies of intestinal microflora. 3. The microbial flora of human small intestinal mucosa and fluids," Gastroenterology 53(6):868-73 (Dec. 1967).
Read, N.W., et al., "Simultaneous measurement of gastric emptying, small bowel residence and colonic filling of a solid meal by the use of the gamma camera," Gut. 27(3):300-8 (Mar. 1986).
Rhodes, J.M., et al., "The lactulose hydrogen breath test as a diagnostic test for small bowel bacterial overgrowth," Scand J Gastroenterol. 14(3):333-6 (1979).
Riordan, S. M., et al., "The lactulose breath hydrogen test and small intestinal bacterial overgrowth," Am. J. Gastroentrol. 91(9):1795-1803 (Sep. 1996).
Rooks et al. Su1940: Methanobrevibacter Smithii is Highly Prominent in the Small Bowel of Rats. Gastroenterology—Proceedings from Digestive Disease Week (2012). 142(5): Suppl 1, p. S-541. Abstract Only.
Rutgeerts, P., et al., "Ileal dysfunction and bacterial overgrowth in patients with Crohn's disease," European J Clin Invest. 11(3):199-206 (Jun. 1981).
Rumessen et al. Carbohydrate Malabsorption: Quantification by Methane and Hydrogen Breath Tests. Scandinavian Journal of Gastroenterology (1994). 29:826-832.
Salminen, S., et al., "Clinical uses of probiotics for stabilizing the guy mucosal barrier: successful strains and future challenges," Antonic Van Leeuwenhoek. 70(2-4):347-58 [1997] (Oct. 1996) (Review).
Sameshima, T., et al., "Effect of intestinal Lactobacillus starter cultures on the behaviour of *Staphylococcus aureus* in fermented sausage," Int. J. Food Microbiol. 41(1):1-7 (May 1998).
Schneider, A., et al., "Value of the 14C-D-xylose breath test in patients with intestinal bacterial overgrowth," Digestion 32(2):86-91 (1985).
Silverman, D..S., et al., "Regional cerebral activity in normal and pathological perception of visceral pain," Gastroenterology. 112(1):64-72 (Jan. 1997).
Soares et al. "Metano no ar Expirado de Criancas com Constipacao Cronica Funcional," Arq. Gastroenterol., vol. 39, No. 1, Jan./Mar. 2002; pp. 66-72.
Soares et al. "Breath methane associated with slow colonic transit time in children with chronic constipation," J. Clin. Gastroenterol. Jul. 2005; vol. 39, No. 6, pp. 512-515.
Spanhaak S., et al., "The effect of consumption of milk fermented by *Lactobacillus casei* strain Shirota on the intestinal microflora and immune parameters in humans," Eur. J. Clin. Nutr. 52(12):899-907 (Dec. 1998).
Strocchi, A., et al., "Detection of malabsorption of low doses of carbohydrate: accuracy of various breath H2 criteria," Gastroenterology 105(5):1404-10 (Nov. 1993).
Sullivan, S.N., "A prospective study of unexplained visible abdominal bloating, " N Z Med J. 107(988):428-30 (Oct. 1994).
Swart, G.R., et al., "$^{13}$C breath test in gastrointestinal practice," Scand. J. Gastroenterol. Suppl. 225:13-18 (1998).
Tannock, G. W, "Probiotic properties of lactic acid bacteria: plenty of scope for R & D," Trends Biotechnol. 15(7):270-74 (Jul. 1997).
The Merck Index (11th Edition), (1989), Entry 5225, p. 844.
Thompson, W.G., et al., "Functional bowel disorders in apparently healthy people." Gastroenterology. 79(2):283-8 (Aug. 1980).
Thompson, W. Grant. "Probiotics for irritable bowel syndrome: a light in the darkness?" Euro. J. of Gastroenterology & Hepatology: Oct. 2001, vol. 13, Issue 10, pp. 1135-1136.
Thompson, W.G., et al., "Functional bowel disorders and functional abdominal pain. Rome II: A multinational consensus document on functional gastrointestinal disorders," Gut 45 Suppl. 2:1143-47 (Sep. 1999).
Tuohy, K.M., et al., "The prebiotic effects of biscuits containing partially hydrolysed guar gum and fructo-oligosaccharides—a human volunteer study", Br J Nutr 86(3):341-8 (Sep. 2001).
Vanderhoof, J.A., et al., "Use of probiotics in childhood gastrointestinal disorders," J Pediatr Gastroenterol Nutr. 27(3):323-32 (Sep. 1998).
Veldhuyzen Van Zanten, S.J., et al., "Design of treatment trials for functional gastrointestinal disorders," Gut. 45 Suppl II:1169-77 (Sep. 1999).
Weaver, G.A., et al., "Incidence of methanogenic bacteria in a sigmoidoscopy population: an association of methanogenic bacteria and diverticulosis," Gut. 27(6):698-704 (Jun. 1986).
Whitehead, W.E., et al., "Effects of stressful life events on bowel symptoms: Subjects with irritable bowel syndrome compared with subjects without bowel dysfunction," Gut 33(6):825-30 (Jun. 1992).
Whitehead, W.E., et al., "Definition of a responder in clinical trials for functional gastrointestinal disorders: reports on a symposium," Gut. 45 Suppl 2:II78-9 (Sep. 1999).
Wolf, B.W. et al., "Safety and tolerance of Lactobacillus reuteri supplementation to a population infected with the human immunodeficiency virus," Food Chem. Toxicol. 36(12):1085-94 (Dec. 1998).

* cited by examiner

C

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: synthetic construct

<400> SEQUENCE: 1
tcctacggga ggcagcagt                                                  19

<210> SEQ ID NO 2
<211> LENGTH: 26
<212> TYPE: DNA
<213> ORGANISM: Artificial Sequence
<220> FEATURE:
<223> OTHER INFORMATION: synthetic construct

<400> SEQUENCE: 2
ggactaccag ggtatctaat cctgtt                                          26

<210> SEQ ID NO 3
<211> LENGTH: 20
<212> TYPE: DNA
<213> ORGANISM: Methanobrevibacter smithii

<400> SEQUENCE: 3
aagggatttg cacccaacac                                                 20

<210> SEQ ID NO 4
<211> LENGTH: 22
<212> TYPE: DNA
<213> ORGANISM: Methanobrevibacter smithii

<400> SEQUENCE: 4
gaccacagtt aggaccctct gg                                              22
```

METHODS OF DIAGNOSIS, SELECTION, AND TREATMENT OF DISEASES AND CONDITIONS CAUSED BY OR ASSOCIATED WITH METHANOGENS

CROSS-REFERENCE TO RELATED APPLICATIONS

This application claims the benefit of priority under 35 U.S.C. §121 as a divisional of U.S. patent application Ser. No. 14/211,197, filed Mar. 14, 2014, and issued as U.S. Pat. No. 9,289,418 on Mar. 22, 2016, which also claims priority under 35 U.S.C. §119(e) to U.S. provisional patent application No. 61/792,687, filed Mar. 15, 2013. The entirety of the aforementioned patent applications are incorporated herein by reference.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The human gastrointestinal (GI) tract is host to a vast number of microorganisms, which include archaea, bacteria, and eukaryotes. To date, at least 70 divisions of bacteria and 13 divisions of archaea have been identified, and their collective genome (the microbiome) is believed to contain 100 times more genes than the human genome (A1,A2). Although the composition and number of microbes in the gut depends on many factors (A3,A4), by adulthood most humans reach an established, relatively stable balance of type, and numbers of microbes that is unique to a given individual (A5). This microbial community is thought to develop with the host by establishing symbiotic relationships which favor their coexistence (A3,A6), such as assisting the host in the breakdown of food for absorption and elimination (A7). While the full breadth of the impact of these gut microbes on the human host will take years to uncover, the complex and often interdependent relationships between gut microbes and the human host have been of increasing scientific interest this past decade, and this interest continues to grow. In particular, there is ample and growing evidence to suggest potential roles for gut microbes in energy homeostasis, inflammation, and insulin resistance (A8-A10), and as a result, gut microbes have been considered as possible causative factors of metabolic conditions and obesity, as well as potential therapeutic targets (A11-A15).

Methanogens are important constituents of gut microbiota that colonize the human intestinal tract. These organisms are not bacteria but archaea and generate methane by utilizing hydrogen and carbon dioxide (from syntrophic hydrogen producing bacteria) [10]. Several decades ago, Miller and Wolin isolated methanogens which were morphologically and physiologically similar to *Methanobrevibacter smithii* from fecal specimens of nine adults demonstrating methane production by enrichment cultures. When examined by immunological methods, these isolates were very closely related to *M. smithii* and unrelated or poorly related to other members of the Methanobacteriaceae family [11]. Utilizing the same morphological and immunological techniques, Weaver et al detected *M. smithii* in tap water enema samples of 70% of their subjects before sigmoidoscopy. A small subset of these patients who underwent breath analysis needed at least $2 \times 10^8$ methanogens/gm dry weight of stool to have detectable breath methane of >6 parts per million (ppm) [12]. However, these studies have not examined subjects with IBS and have not been replicated using molecular techniques such as PCR.

This distinct group grows primarily under anaerobic conditions, and produces methane ($CH_4$) as a byproduct of fermentation. Methanogens are unique in that their metabolism increases in the presence of products from other gut microbes (A16), as they scavenge hydrogen and ammonia as substrates for the generation of methane (A17,A18). Once absorbed into systemic circulation, methane is cleared via the lungs. The majority of methanogens found in the human gut are from the genus *Methanobrevibacter*; predominantly *Methanobrevibacter smithii* (A7). *M. smithii* is found in 70% of human subjects, and analysis of expiratory methane by lactulose breath testing can serve as an indirect measure of methane production (A7,A19). A minority of subjects (15%) produce large quantities of methane early in the breath test, suggesting a greater methane potential (A20), and increased methane production on breath test correlates with increased levels of *M. smithii* in stool, as determined by quantitative PCR (qPCR) (A20,A21).

Introduction of both a *Bacteroides* species (*Bacteroides thetaiotaomicron*) and *M. smithii* into germ-free mice resulted in greater body weights than with *B. thetaiotaomicron* alone (A22), and methanogens have been shown to increase the capacity of polysaccharide-metabolizing bacteria to digest polyfructose-containing glycans in the colons of germ-free mice (A22), suggesting that methanogens may play a role in caloric harvest. In humans, the inventors have recently found that increased methane on breath test is associated with a higher average BMI, both in normal population and in obese subjects. In the obese population, methane was associated with a remarkable 6.7 kg/m2 greater BMI compared to non-methane controls (P<0.05) (A23). While these data are suggestive of a role for methanogens in caloric harvest and weight gain in humans, this is weakened by the fact that, to date, colonization with methanogens has only been demonstrated in the large bowel (A24-A26).

Therefore, as described herein the inventors tested and compared weight gain and the location and extent of *M. smithii* colonization in the GI tracts of rats under different dietary conditions. Also described herein, the inventors examine the importance of *Methanobrevibacter smithii* as a determinant of methane production in the breath of humans using quantitative-polymerase chain reaction (PCR) from stool of IBS patients with and without detectable methane on breath testing.

Obesity constitutes a significant and rapidly increasing public health challenge and is associated with increased risks for coronary artery disease, hypertension, stroke, type 2 diabetes, certain cancers, and premature death (B1, B2). Elucidating mechanisms contributing to the development of obesity is central to defining preventive approaches. Research has begun to define the relationship between gut flora and metabolism (B3-B5). Alterations in the relative abundance of Bacteroidetes and Firmicutes have been linked to changes in metabolism and weight increases both in mice (B6) and humans (B4). Cocolonization with the methanogenic archaea, *Methanobrevibacter smithii*, results in a greater weight gain in germ-free animals than infection with *B. thetaiotaomicron* alone (B7).

Accordingly, there exists a need for methods for determining the presence of methanogens, and their cause and/or association with various diseases and conditions, and selecting and/or administering an appropriate treatment for those diseases and conditions, such as obesity, pre-diabetes diabetes, diabetes, insulin resistance, glucose intolerance, constipation, fatty liver, Crohn's disease and ulcerative colitis, to name a few.

SUMMARY OF THE INVENTION

The following embodiments and aspects thereof are described and illustrated in conjunction with compositions and methods which are meant to be exemplary and illustrative, not limiting in scope.

Various embodiments provide for a method, comprising subjecting a biological sample from a subject to analysis for methanogen quantity; comparing the methanogen quantity to a reference value; and selecting a first therapy for the subject if the methanogen quantity is higher than the reference value based on the recognition that the first therapy is appropriate for subjects who have a methanogen quantity higher than the reference value, or selecting a second therapy for the subject if the methanogen quantity is lower than the reference value based on the recognition that the second therapy is appropriate for subjects who have a methanogen quantity lower than the reference value, wherein the subject has or is suspected to have a disease or condition caused by or associated with having a high methanogen quantity or a disease or condition caused by or associated with having a low methanogen quantity.

Various embodiments of the present invention provide for a method, comprising subjecting a biological sample from a subject to analysis for methanogen quantity; comparing the methanogen quantity to a reference value; and selecting a first therapy for the subject if the methanogen quantity is higher than the reference value based on the recognition that the first therapy is appropriate for subjects who have a methanogen quantity higher than the reference value, or selecting a second therapy for the subject if the methanogen quantity is lower than the reference value based on the recognition that the second therapy is appropriate for subjects who have a methanogen quantity lower than the reference value, wherein the subject desires a determination of susceptibility to having a disease or condition caused by or associated with having a high methanogen quantity or a disease or condition caused by or associated with having a low methanogen quantity.

In various embodiments, the method can further comprise providing the biological sample. In various embodiments, the method can further comprise administering the selected therapy.

In various embodiments, the method can further comprise subjecting the biological sample to analysis for a quantity of a methanogen syntrophic microorganism. In various embodiments, the methanogen syntrophic microorganism can be a hydrogen-producing microorganism. In various embodiments, the method can further comprise selecting a third therapy to inhibit the growth of the methanogen syntrophic microorganism. In various embodiments, the method can further comprise administering the third therapy.

In various embodiments of the method, the biological sample can be selected from stool, mucosal biopsy from a site in the gastrointestinal tract, aspirated liquid from a site in the gastrointestinal tract, or combinations thereof. In various embodiments of the method, the site in the gastrointestinal tract can be mouth, stomach, small intestine, large intestine, anus or combinations thereof. In various embodiments of the method, the site in the gastrointestinal tract can be duodenum, jejunum, ileum, or combinations thereof. In various embodiments of the method, the site in the gastrointestinal tract can be cecum, colon, rectum, anus or combinations thereof. In various embodiments of the method, the site in the gastrointestinal tract can be ascending colon, transverse colon, descending colon, sigmoid flexure, or combinations thereof.

In various embodiments of the method, the analysis for methanogen quantity can be by using quantitative polymerase chain reaction (qPCR).

In various embodiments of the method, the disease or condition caused by or associated with having the high methanogen quantity can be selected from the group consisting of obesity, constipation, fatty liver (NASH), pre-diabetes, diabetes, insulin resistance, glucose intolerance and combinations thereof.

In various embodiments of the method, the disease or condition caused by or associated with having the low methanogen quantity can be Crohn's disease or ulcerative colitis.

In various embodiments of the method, the methanogen can be from the genus *Methanobrevibacter*. In various embodiments, the *Methanobrevibacter* can be selected from the group consisting of *M. acididurans, M. arboriphilus, M. curvatus, M. cuticularis, M. filiformis, M. gottschalkii, M. millerae, M. olleyae, M. oralis, M. ruminantium, M. smithii, M. thaueri, M. woesei, M. wolinii* and combinations thereof. In various embodiments, the *Methanobrevibacter* can be *Methanobrevibacter smithii* (*M. Smithii*).

In various embodiments of the method, the reference value can be about 10,000 per ml of the biological sample.

In various embodiments of the method, the first therapy can be an antibiotic or a combination of two or more antibiotics. In various embodiments, the antibiotic or the combination of two or more antibiotics can be selected from the group consisting of rifaximin, neomycin, vancomycin, and metronidazole. In various embodiments, the antibiotic can be rifaximin. In various embodiments, the antibiotic can be neomycin. In various embodiments, the antibiotic can be vancomycin. In various embodiments, the antibiotic can be metronidazole. In various embodiments, the combination of two or more antibiotics can be rifaximin and neomycin, or rifaximin and metronidazole.

In various embodiments of the method, the first therapy can be a probiotic capable of inhibiting the methanogen growth.

In various embodiments of the method, the first therapy can be a reduced-calorie diet.

In various embodiments of the method, the first therapy can be a reduced-fat diet.

In various embodiments of the method, the first therapy can be an elemental diet.

In various embodiments of the method, the first therapy can be a statin. In various embodiments, the statin can be selected from the group consisting of atorvastatin, fluvastatin, lovastatin, pitavastatin, pravastatin, rosuvastatin, simvastatin, and combinations thereof.

In various embodiments of the method, the disease or condition is obesity and the first therapy can be an anti-obesity drug. In various embodiments, the anti-obesity drug can be phentermine, phentermine/topiramate, xenical, lorcaserin, or rimonabant.

In various embodiments of the method, the disease or a condition can be selected from the group consisting of pre-diabetes, diabetes, insulin resistance, and glucose intolerance, and the first therapy can be selected from the group consisting of alpha-glucosidase inhibitors, amylin analog, dipeptidyl peptidase-4 inhibitor, GLP1 agonist, meglitinide, sulfonylurea, biguanide, thiazolidinedione (TZD), insulin, and combinations thereof. In various embodiments, the alpha-glucosidase inhibitors can be select from the group consisting of acarbose, miglitol and combinations thereof. In various embodiments, the amylin analog can be pramlintide. In various embodiments, the dipeptidyl peptidase-4 inhibitor can be selected from the group consisting of Saxagliptin, Sitagliptin, Vildagliptin, Linagliptin, Alogliptin, or combinations thereof. In various embodiments, the GLP1 agonist can be selected from the group consisting of liraglutide exenatide, exenatide extended release, or combinations thereof. In various embodiments, the meglitinide can be selected from the group consisting of nateglinide, repaglinide, and combinations thereof. In various embodiments, the sulfonylurea can be selected from the group consisting of chlorpropamide, Glimepiride, Glipizide, Glyburide, Tolazamide, Tolbutamide and combinations thereof. In various embodiments, the biguanide can be selected from the group consisting of Metformin, Riomet, Glucophage, Glucophage extended release, Glumetza, and combinations thereof. In various embodiments, the thiazolidinedione can be selected from the group consisting of Rosiglitazone, Pioglitazone and combinations thereof. In various embodiments, the insulin can be selected from the group consisting of Aspart, Detemir, Glargine, Glulisine, Lispro, and combinations thereof.

In various embodiments of the method, the disease or a condition can be selected from the group consisting of pre-diabetes, diabetes, insulin resistance, and glucose intolerance, and the first therapy can be selected from the group consisting Glipizide/Metformin, Glyburide/Metformin, Pioglitazone/Glimepiride, Pioglitazone/Metformin, Repaglinide/Metformin, Rosiglitazone/Glimepiride, Rosiglitazone/Metformin, Saxagliptin/Metformin, Sitagliptin/Simvastatin, Sitagliptin/Metformin, Linagliptin/Metformin, Alogliptin/Metformin, Alogliptin/Pioglitazone, bromocriptine, welchol, and combinations thereof.

In various embodiments of the method, the disease or condition can be constipation, and the first therapy can be selected from the group consisting of laxative, diet, guanylate cyclase C agonist, a serotonin agonist, and combinations thereof. In various embodiments, the guanylate cyclase C agonist can be linaclotide. In various embodiments, the serotonin agonist can be prucalorpride, tegaserod or combinations thereof.

In various embodiments of the method, the disease or condition can be fatty liver, and the first therapy can be metformin.

In various embodiments of the method, the disease or condition can be Crohn's disease and the second therapy can be administering a methanogen.

In various embodiments, the methanogen can be from the genus *Methanobrevibacter*. In various embodiments, the *Methanobrevibacter* can be selected from the group consisting of *M. acididurans, M. arboriphilus, M. curvatus, M. cuticularis, M. filiformis, M. gottschalkii, M. millerae, M. olleyae, M. oralis, M. ruminantium, M. smithii, M. thaueri, M. woesei, M. wolinii* and combinations thereof.

In various embodiment, the *Methanobrevibacter* can be *Methanobrevibacter smithii* (*M. Smithii*).

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
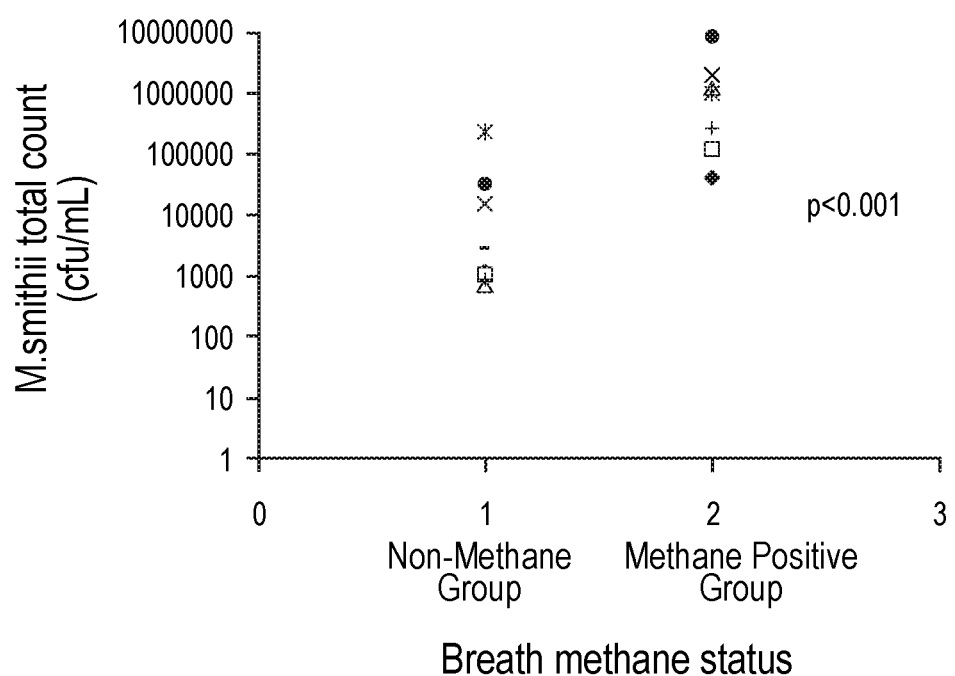
FIG. 1 depicts *M. Smithii* counts in methane and non-methane producers in stool in accordance with various embodiments of the present invention.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease or condition, preventing or inhibiting the disease condition from worsening, curing the disease condition and prolonging a patient's life or life expectancy.

"Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus adult and newborn subjects, as well as fetuses, whether male or female, are intended to be including within the scope of this term.

"Therapeutically effective amount" as used herein refers to that amount which is capable of achieving beneficial results in a patient with a high quantity of methanogens or a patient with a low quantity or nonexistence of methanogens. A therapeutically effective amount can be determined on an individual basis and will be based, at least in part, on consideration of the physiological characteristics of the mammal, the type of delivery system or therapeutic technique used and the time of administration relative to the progression of the disease or condition.

"Treatment" and "treating," as used herein refer to both therapeutic treatment and prophylactic or preventative measures, wherein the object is to prevent, slow down and/or lessen the disease even if the treatment is ultimately unsuccessful.

Described herein, the inventors demonstrated that *Methanobrevibacter smithii* is likely the important methanogen responsible for breath methane in subjects with IBS. Furthermore, *M. smithii* levels and relative proportions in stool correlate with the degree of methane production suggesting this may be the major methanogen responsible for methane during breath testing in humans. Finally, this is the first study to demonstrate by qPCR that *M. smithii* is important in C-IBS subjects with methane on LBT.

Recent literature suggests a role of methanogenic gastrointestinal microbiota in the pathophysiology of functional gastrointestinal disorder such as IBS. Specifically, methane gas on LBT is associated with a constipation phenotype [5, 6, 7]. The inventors' group has shown that methane is not an inert gas as previously thought; but slows intestinal transit [14]. In an in-vivo study on 5 dogs, infusing methane through mid-small bowel fistula reduced proximal small bowel motility by an average of 59% [14]. The presence of breath methane has also been associated with significant slowing of intestinal transit in human studies [8, 15, 16]. Among patients with IBS, it has been confirmed in a multitude of publications that methane on lactulose breath testing is almost universally associated with constipation predominant disease [5, 6, 7, 8]. However, evaluation of stool in such patients in order to determine the source of methane has never been attempted in IBS.

Described herein, the inventors established that *Methanobrevibacter smithii* is present ubiquitously in the stool of IBS patients. However, patients with methane-positive breath test harbor significantly greater quantity of *M. smithii* as compared to the methane negative ones. These patients also have higher proportions of *M. smithii* in their stool relative to other bacteria. The higher the count or relative proportion of *M. smithii* in stool, the greater the degree of breath methane. This implies that stool quantitative-PCR is a much more sensitive tool than breath analysis in order to detect intestinal methanogens.

Interestingly, methanogens alone may not be problematic. In this study, most subjects had detectable *M. smithii* in their stool. However, the level of *M. smithii* may be the issue. Based on this study, methane on the breath appears to be detectable when the level of *M. smithii* exceeds $4.2 \times 10^5$ copies per gm of wet stool or 1.2% of the total stool bacteria. This is important since in the original description of methane on breath and constipation IBS, not all constipation predominant IBS subjects had methane. However, nearly all methane subjects were constipated. Combined, these findings suggest that stool testing by qPCR may identify a threshold for producing constipation that a breath test is not sensitive enough to detect.

Also described herein, the threshold of *M. smithii* to cause detectable methane on breath analysis was much smaller than that reported earlier by Weaver et al [12]. This difference is likely due to the use of differing techniques. In the study by Weaver, et al, methanogens were cultured from the stool sample and identification as *M. smithii* was based on morphological and immunological methods. Handling and culture of stool for methanogens can be difficult as the organisms are anaerobic. Exposure of the stool sample to air might harm the organisms limiting their growth. In the case of q-PCR, handling is not problematic since PCR will detect both viable and non-viable organisms.

These data may have therapeutic and clinical significance as elimination of methanogens by non-absorbable antibiotics can significantly improve gut symptoms [17, 18]. In methane producers with constipation predominant IBS, neomycin resulted in 44.0±12.3% vs 5.0±5.1% improvement in constipation as compared to placebo that correlated well with elimination of methane on follow up breath testing [19]. In a retrospective study, combination of rifaximin and neomycin for 10 days resulted in significantly greater reduction in methane (87%) and constipation symptoms (85%) as compared to neomycin (33% and 63%, respectively) or rifaximin (28% and 56%, respectively) alone [20].

The inventors observed positive trends for association between *M. smithii* and constipation. The inventors' results suggest that *M. smithii* is the predominant methanogenic archaeabacteria in the gut of C-IBS patients responsible for methane on breath test. This is supported by the correlation between *M. smithii* level in stool and methane AUC on breath testing.

Further described herein the inventors demonstrate for the first time that colonization of the rat gut with the methanogen *M. smithii* is not limited to the large bowel, but rather extends to the small bowel, including the ileum, jejunum, and duodenum. In fact, the inventors found that the levels of *M. smithii* were higher in the small bowel than in the large bowel, with the most elevated levels seen in the ileum. Moreover, the inventors found that switching rats to a high-fat diet resulted both in increased levels of *M. smithii* in stool, and in increased levels of *M. smithii* in all bowel segments tested. Most significantly, the inventors found that rats which gained more weight had higher stool levels of *M. smithii* than rats which gained less weight, and that the extent of colonization of the bowel with *M. smithii* colonization also corresponded with weight gain in these rats, irrespective of diet. Taken together, these findings support that the level and extent of colonization of the intestinal tract with *M. smithii* is predictive of the degree of weight gain in this animal model.

It is becoming increasingly understood that gut microbes play roles in and affect host metabolism and energy homeostasis, and the inventors believe that they contribute to the development of metabolic disorders and obesity. Through the production of enzymes, gut microbes assist the host in: utilizing nondigestible carbohydrates and host-derived glycoconjugates, resulting in increased short-chain fatty acid (SCFA) production; deconjugating and dehydroxylating bile acids, which alters the solubilization and absorption of dietary lipids; and cholesterol reduction and biosynthesis of vitamins from the K and B group, isoprenoids and amino acids such as lysine and threonine (A1,A11,A28,A29). Gut microbes have also been suggested to affect intestinal transit times, and to contribute to the chronic low-grade inflammation and insulin resistance that are associated with obesity via effects on the endotoxin toll-like receptor 4 axis and intestinal barrier function (A14,A30). These data support a role for gut microbes in contributing to weight gain by the host, which validates the inventors' finding that weight gain in the inventors' animal model was more dependent on the degree and extent of *M. smithii* colonization of the gut than on dietary fat content.

Several lines of evidence support that methanogens may play a specific role in host metabolism and energy homeostasis. Methanogens such as *M. smithii*, which is the most common methanogen in the human gut, produce methane through anaerobic fermentation (A17,A18), and remove hydrogen atoms and accelerate the fermentation of polysaccharides and carbohydrates (A22). This increases the production of SCFAs, which are subsequently absorbed in the intestines and serve as an additional energy source for the host (A11). This more efficient energy extraction may lead to weight gain and ultimately contribute to obesity (A32). One potential mechanism for this is through effects of SCFAs on G protein-coupled receptors, for which they act as ligands. The G protein-coupled receptor Gpr41 is expressed in the intestine, colon, and adipocytes, and stimulates the expression of the adipokine leptin and the peptide tyrosine-tyrosine (peptide-YY), which both influence energy metabolism, and also affect appetite levels/satiety. In addition, modulation of plasma SCFAs has been linked to decreases of inflammatory markers in insulin-resistant human subjects (A33,A34), suggesting a potential effect on the chronic low-grade inflammation associated with obesity. Interestingly, in a recent human study the inventors found that during a 75 g oral glucose tolerance test, methane-producing subjects (i.e., those with increased methane on breath test) had greater serum glucose area-under-the-curve than non-methane subjects, despite having comparable BMIs and baseline insulin resistance (homeostatic model assessment-insulin resistance), suggesting that intestinal methane-producing subjects may have impaired glucose tolerance when challenged with a high carbohydrate load, and thus a higher susceptibility to hyperglycemia, than non-methane subjects (R. Mathur et al., data not shown). A final potential mechanism whereby methanogens may affect energy extraction by the host is by slowing gut motility. Among human irritable bowel syndrome patients, the inventors found that those with methane on breath test are more likely to have constipation as a predominant symptom subtype (A19,A35), and that the amount of methane produced is related to the degree of constipation, as measured by Bristol Stool Score, and frequency of bowel movements (A35). Methane is also associated with other constipation disorders (A36,A37). In an in vivo animal study, the inventors' group demonstrated that infusion of methane into the small intestine resulted in slowing of small intestinal transit by 59% (A38). That slowing of intestinal transit may be associated with greater BMI is demonstrated by a study by the gastroparesis consortium, which showed that subjects with extreme slow motility (gastroparesis) had higher BMIs (A39), and by a study of ultrashort bowel patients, in which the inventors' group found that slowing the gut with exenatide resulted in resolution of diarrhea, nutritional deficiencies and the need for chronic parenteral nutrition, and was accompanied by weight gain (A40). Taken together, these represent several potential mechanisms by which the increased *M. smithii* colonization could contribute to the concomitant weight gain the inventors observed in these rats.

To date, methanogens have been identified primarily in the left colon (A24-A26), and it has been argued that alterations to a gut microbial population not known to occur outside of the large bowel is unlikely to be a significant direct cause of weight gain. The inventors' results demonstrate for the first time that in the rat, not only does colonization with *M. smithii* occur in the small bowel, but that *M. smithii* levels in the duodenum, jejunum, and ileum are in fact higher than in the cecum or left colon, with highest levels in the ileum. Moreover, the degree of weight gain in these animals corresponded with the number of bowel segments colonized, and the inventors believe that the extent of colonization of the intestine with *M. smithii* is predictive of, and contribute to, weight gain.

In conclusion, the inventors' results demonstrate for the first time that colonization with the methanogen *M. smithii* is not confined to the large intestine, but also occurs in the small bowel. Moreover, in this rat model, the inventors found that the levels and extent of small intestinal colonization with *M. smithii* correlated with, and were predictive of, the degree of weight gain, irrespective of dietary fat content.

Also described herein, the inventors demonstrate clear associations between the presence of both methane and hydrogen on breath testing and increased BMI as well as increased percent body fat in an analysis of nearly 800 subjects. This study is the first of its kind to identify the production of methane and hydrogen as an indicator of higher BMI and fat content in human subjects.

Obesity is a public health problem and is undoubtedly multifactorial. Dysregulations are seen in multiple areas of energy intake, expenditure, and storage. There is growing interest in the potential role of gut flora in the pathogenesis of obesity. Research by Gordon, Backhed, and others (B3-B7) have shown an intriguing relationship between microbial flora and weight gain in mouse models, including an association between alterations in the relative abundance of Firmicutes vs Bacteroidetes in the gut and potentially enhanced nutritional harvest (B3). Intestinal flora have been implicated in many mechanisms that may contribute to weight gain, including enhanced lipopolysaccharide production leading to insulin resistance (B5), suppression of fasting-induced adipose factor (B14), suppression of AMP-activated protein kinase-driven fatty acid oxidation in the liver (B15), incretin regulation (B16), and increased SCFA production and absorption, thereby providing increased lipogenic substrates to the host (B17). Increased methanogens have also been observed in the cecal flora of Ob/Ob mice (B3). The inventors believe that this large-scale human study described herein shows a role for methanogens, and specifically *M. smithii*, in human obesity.

The human GI tract is colonized by up to $10^{12}$ microbial species, including bacteria and archaea, of which *M. smithii* is the most abundant methane-producing organism (B9). The inventors show herein that methane-positive individuals have *M. smithii* in the GI tract. The inventors have shown that increased methane on breath testing is associated with higher levels of *M. smithii* in stool, and that methane-positive obese subjects have an average 6.7 kg/m$^2$ greater BMI than methane-negative obese controls (B11). Although *M. smithii* was originally thought to inhabit only the large bowel, weakening the likelihood that it could play a significant role in caloric harvest and weight gain, the inventors show herein using a rat model that *M. smithii* colonization in fact occurs throughout the small intestine. Importantly, the number of bowel segments colonized with *M. smithii* was directly related to the degree of weight gain in this rat model and was further enhanced in the presence of a high-fat diet.

The inventors believe that the role of *M. smithii* in weight gain in animals is facilitative and involves a syntrophic relationship with other microbes, whereby *M. smithii* scavenges hydrogen produced by syntrophic organisms for its hydrogen-requiring anaerobic metabolism, producing methane as a byproduct. This scavenging of hydrogen allows the syntrophic organisms to be more productive, increasing SCFA production and availability of calories for the host (B8). The inventors' results support this—the presence of both hydrogen and methane on breath test, but not either methane or hydrogen alone, is associated with higher BMI and percent body fat, perhaps because these subjects have an abundance of hydrogen to fuel methane production.

In addition, methane itself (in gaseous form as generated by intestinal methanogens) could also contribute to enhanced energy harvest. The inventors previously noted an association between breath methane and constipation (constipation-irritable bowel syndrome) in human subjects (B13) and, using an in vivo animal model, demonstrated that methane gas directly slows transit in the gut by 59% (B19). The inventors believe that the slowing of transit could result in greater time to harvest nutrients and absorb calories, representing another potential mechanism for weight gain.

Although the mean age of the methane producers was higher than that of the controls, the results retained significance, even when controlling for age as a confounding variable. Furthermore, there is no evidence to suggest that methane production increases with age but rather plateaus in adulthood (B20), making it unlikely that age could affect the study findings. The inventors show herein that diet can affect overall intestinal flora and *M. smithii* levels in animal models. The inventors' study does not account for dietary differences among subjects. However, given the large sample size, these individual variations may be mitigated between groups.

In summary, the inventors' study demonstrates for the first time that individuals with both methane and hydrogen on a breath test have higher BMIs and percent body fat. The inventors believe that this is due to excessive colonization with the hydrogen-requiring methanogen *M. smithii*, which enhances energy harvest and delivery of nutrients to the host organism through syntrophic relationships with other microbes.

Various embodiments of the present invention are based, at least in part, on these findings.

Various embodiments of the present invention provide for a method for selecting and/or administering a therapy for a subject who has or is suspected to have a disease or condition caused by or associated with having a high methanogen quantity or a disease or condition caused by or associated with having a low methanogen quantity. The method comprises subjecting a biological sample from a subject to analysis for methanogen quantity; comparing the methanogen quantity to a reference value; and selecting a first therapy for the subject if the methanogen quantity is higher than the reference value based on the recognition that the first therapy is appropriate for subjects who have a methanogen quantity higher than the reference value, or selecting a second therapy for the subject if the methanogen quantity is lower than the reference value based on the recognition that the second therapy is appropriate for subjects who have a methanogen quantity lower than the reference value, wherein the subject has or is suspected to have a disease or condition caused by or associated with having a high methanogen quantity or a disease or condition caused by or associated with having a low methanogen quantity. First therapy and second therapy as used in this context do not refer to administering two therapies, it is simply to provide a distinctions between two types of therapies. The first therapy is a therapy that is appropriate for treating subjects who have high quantities of methanogens. The second therapy is a therapy that is appropriate for treatment subject who have low or non-detectable quantities of methanogens.

In various embodiments, the method further comprises identifying the subject who has or is suspected to have a disease or condition caused by or associated with having a high methanogen quantity or a disease or condition caused by or associated with having a low methanogen quantity.

In various embodiments, the method further comprises obtaining or providing the biological sample. In various embodiments, the method further comprises administering the selected therapy.

In various embodiments, the method further comprises subjecting the biological sample to analysis for a quantity of a methanogen syntrophic microorganism. In various embodiments, the methanogen syntrophic microorganism is a hydrogen-producing microorganism. In various embodiments, the method further comprises selecting a third therapy to inhibit the growth of the methanogen syntrophic microorganism. In various embodiments, the method further comprises administering the third therapy. In various embodiments, the third therapy and the first therapy can be the same or same type of therapy.

Various embodiments provide for a method for selecting a therapy for a subject who desires a determination of susceptibility to having a disease or condition caused by or associated with having a high methanogen quantity or a disease or condition caused by or associated with having a low methanogen quantity. The method comprises subjecting a biological sample from a subject to analysis for methanogen quantity; comparing the methanogen quantity to a reference value; and selecting a first therapy for the subject if the methanogen quantity is higher than the reference value based on the recognition that the first therapy is appropriate for subjects who have a methanogen quantity higher than the reference value, or selecting a second therapy for the subject if the methanogen quantity is lower than the reference value based on the recognition that the second therapy is appropriate for subjects who have a methanogen quantity lower than the reference value, wherein the subject desires a determination of susceptibility to having a disease or condition caused by or associated with having a high methanogen quantity or a disease or condition caused by or associated with having a low methanogen quantity.

In various embodiments, the method further comprises identifying the subject who desires a determination of susceptibility to having a disease or condition caused by or associated with having a high methanogen quantity or a disease or condition caused by or associated with having a low methanogen quantity In various embodiments, the method further comprises providing the biological sample.

In various embodiments, the method further comprises administering the selected therapy.

In various embodiments, the method further comprises subjecting the biological sample to analysis for a quantity of a methanogen syntrophic microorganism. In various embodiments, the methanogen syntrophic microorganism is a hydrogen-producing microorganism. In various embodiments, the method further comprises selecting a third therapy to inhibit the growth of the methanogen syntrophic microorganism. In various embodiments, the method further comprises administering the third therapy.

Various embodiments of the present invention provide for a method for treating a subject who has or is suspected to have a disease or condition caused by or associated with having a high methanogen quantity or a disease or condition caused by or associated with having a low methanogen quantity. The method comprises subjecting a biological sample from a subject to analysis for methanogen quantity; comparing the methanogen quantity to a reference value; selecting a first therapy for the subject if the methanogen quantity is higher than the reference value based on the recognition that the first therapy is appropriate for subjects who have a methanogen quantity higher than the reference value, or selecting a second therapy for the subject if the methanogen quantity is lower than the reference value based on the recognition that the second therapy is appropriate for subjects who have a methanogen quantity lower than the reference value; and administering the selected therapy to the patient to treat the disease or condition, wherein the subject has or is suspected to have a disease or condition caused by or associated with having a high methanogen quantity or a disease or condition caused by or associated with having a low methanogen quantity.

First therapy and second therapy as used in this context do not refer to administering two therapies, it is simply to provide a distinctions between two types of therapies. The first therapy is a therapy that is appropriate for treating subjects who have high quantities of methanogens. The second therapy is a therapy that is appropriate for treatment subject who have low or non-detectable quantities of methanogens.

In various embodiments, the method further comprises identifying the subject who has or is suspected to have a disease or condition caused by or associated with having a high methanogen quantity or a disease or condition caused by or associated with having a low methanogen quantity, for treatment.

In various embodiments, the method further comprises obtaining or providing the biological sample.

In various embodiments, the method further comprises subjecting the biological sample to analysis for a quantity of a methanogen syntrophic microorganism. In various embodiments, the methanogen syntrophic microorganism is a hydrogen-producing microorganism. In various embodiments, the method further comprises selecting a third therapy to inhibit the growth of the methanogen syntrophic microorganism. In various embodiments, the method further comprises administering the third therapy. In various embodiments, the third therapy and the first therapy can be the same or same type of therapy.

Various embodiments of the present invention provide for a method for treating a subject who has or is suspected to have a disease or condition caused by or associated with having a high methanogen quantity or a disease or condition caused by or associated with having a low methanogen quantity. The method comprises administering a first therapy to the subject who has or is determined to have a methanogen quantity that is higher than a reference value based on the recognition that the first therapy is appropriate for subjects who have a methanogen quantity higher than the reference value, or administering a second therapy to the subject who has or is determined to have a methanogen quantity that is lower than the reference value based on the recognition that the second therapy is appropriate for subjects who have a methanogen quantity lower than the reference value.

First therapy and second therapy as used in this context do not refer to administering two therapies, it is simply to provide a distinctions between two types of therapies. The first therapy is a therapy that is appropriate for treating subjects who have high quantities of methanogens. The second therapy is a therapy that is appropriate for treatment subject who have low or non-detectable quantities of methanogens.

In various embodiments, the method further comprises identifying the subject who has or is suspected to have a disease or condition caused by or associated with having a high methanogen quantity or a disease or condition caused by or associated with having a low methanogen quantity, for treatment.

In various embodiments, the subject has or is determined to have a high quantity of a methanogen syntrophic microorganism. In various embodiments, the methanogen syntrophic microorganism is a hydrogen-producing microorganism. In various embodiments, the method further comprises selecting a third therapy to inhibit the growth of the methanogen syntrophic microorganism. In various embodiments, the method further comprises administering the third therapy. In various embodiments, the third therapy and the first therapy can be the same or same type of therapy.

Various embodiments of the present invention provide for a method of diagnosing disease or condition caused by or associated with having a high methanogen quantity or a disease or condition caused by or associated with having a low methanogen quantity. The method comprises subjecting a biological sample from a subject to analysis for methanogen quantity; comparing the methanogen quantity to a reference value; and determining that the subject has the disease or condition if the methanogen quantity is higher than the reference value, or determining that the subject does not have the disease or condition if the methanogen quantity is lower than the reference value.

In various embodiments, the method further comprises identifying the subject for diagnosis. In various embodiments, the method further comprises obtaining or providing the biological sample.

In various embodiments, the method further comprises subjecting the biological sample to analysis for a quantity of a methanogen syntrophic microorganism. In various embodiments, the methanogen syntrophic microorganism is a hydrogen-producing microorganism.

Various embodiments of the present invention provide for a method of diagnosing a susceptibility to a disease or condition caused by or associated with having a high methanogen quantity. The method comprises subjecting a biological sample from a subject to analysis for methanogen quantity; comparing the methanogen quantity to a reference value; and determining that the subject is susceptible to the disease or condition caused by or associated with having a high methanogen quantity if the methanogen quantity is higher than the reference value, or determining that the subject is not susceptible to the disease or condition caused by or associated with having a high methanogen quantity if the methanogen quantity is lower than the reference value.

Various embodiments of the present invention provide for a method of diagnosing a susceptibility to a disease or condition caused by or associated with having a low methanogen quantity. The method comprises subjecting a biological sample from a subject to analysis for methanogen quantity; comparing the methanogen quantity to a reference value; and determining that the subject is susceptible to the disease or condition caused by or associated with having a low methanogen quantity if the methanogen quantity is lower than the reference value, or determining that the subject is not susceptible to the disease or condition caused by or associated with having a low methanogen quantity if the methanogen quantity is higher than the reference value.

In various embodiments, the method further comprises identifying the subject for diagnosis. In various embodiments, the method further comprises obtaining or providing the biological sample.

In various embodiments, the method further comprises subjecting the biological sample to analysis for a quantity of a methanogen syntrophic microorganism. In various embodiments, the methanogen syntrophic microorganism is a hydrogen-producing microorganism.

In various embodiments, the invention provide for systems comprising components that are adapted to perform the methods of the invention described herein.

Reference Value

In various embodiments, the reference value is about 10,000 per ml of the biological sample. Thus, high methanogen quantity is a quantity greater than 10,000 per ml of the biological sample, and a low methanogen quantity is a quantity less than 10,000 per ml of the biological sample. In some embodiments, the reference value is about 5,000, 6,000, 7,000, 8,000, 9,000, 10,000, 11,000, 12,000, 13,000, 14,000, 15,000, or 20,000 per ml of the biological sample. Thus, in some embodiments, high methanogen quantity is a quantity greater than about 5,000, 6,000, 7,000, 8,000, 9,000, 10,000, 11,000, 12,000, 13,000, 14,000, 15,000, or 20,000 per ml of the biological sample, and a low methanogen quantity is a quantity less than 5,000, 6,000, 7,000, 8,000, 9,000, 10,000, 11,000, 12,000, 13,000, 14,000, 15,000, or 20,000 per ml of the biological sample. In some embodiments, these amounts can be per mg of the biological sample.

In various embodiments, the reference value, particularly when used to determine a low methanogen quantity is about 4,000 per ml of the biological sample. Thus, low methanogen quantity is a quantity lower than 4,000 per ml of the biological sample. In some embodiments, the reference value is about 3,000, 2,000, 1,000, or 500 per ml of the biological sample. Thus, in some embodiments, low methanogen quantity is a quantity less than 3,000, 2,000, 1,000, or 500 per ml of the biological sample. In some embodiments, these amounts can be per mg of the biological sample.

The reference value can depend on the type of disease or condition that will be determined. Different types of diseases and conditions may have a different reference values.

In reference value can established from biological samples from a healthy subject.

For example, if the biological sample is stool, then the reference value can be obtained from the stools of a healthy subject. In other embodiments, the reference value is the average methanogen count for the same type of biological sample from a population of healthy subjects. In other embodiments, the reference value is the average plus one or two standard deviations of average methanogen count for the same type of biological sample from a population of healthy subjects. In some embodiments, the population of healthy subjects can range from at least three healthy individuals to 25 healthy individuals, and even more than 50 healthy individuals.

Subjects

The subject from whom a biological sample is obtained can be a subject who has or is suspected to have a disease or condition caused, at least in part, by having high methanogen quantities or associated with having high methanogen quantities. Examples of these subjects include but are not limited to those who are or who are suspected to be overweight, obese, constipated, pre-diabetic, diabetic, insulin resistant, or glucose intolerant, or to have fatty liver (NASH).

The subjects from whom a biological sample is obtained can be a subject who has or is suspected to have a disease or condition caused, at least in part, by having low methanogen quantities or associated with having low methanogen quantities. Examples of these subjects include but are not limited to subjects who have or are suspected to have Crohn's disease or ulcerative colitis.

In certain embodiments the subject from whom a biological sample is obtained can be a subject who desires to know whether he or she is susceptible to a disease or condition caused, at least in part, by having high methanogen quantities or associated with having high methanogen quantities. Examples of these subjects include but are not limited to those who desires to know whether he or she are susceptible to being overweight, obese, constipated, pre-diabetic, diabetic, insulin resistant, or glucose intolerant, or to have fatty liver (NASH).

The subjects from whom a biological sample is obtained can be a subject who desires to know whether he or she is susceptible to a disease or condition caused, at least in part, by having low methanogen quantities or associated with having low methanogen quantities. Examples of these subjects include but are not limited to subjects who desires to know whether he or she is susceptible to having Crohn's disease or ulcerative colitis.

Biological Samples

The biological sample that is analyzed by methods of the present invention can be stool, mucosal biopsy from a site in the gastrointestinal tract, or aspirated liquid from a site in the gastrointestinal tract. In various embodiments, the site in the gastrointestinal tract is mouth, stomach, small intestine, large intestine, or anus. In various embodiments, the site in the gastrointestinal tract is duodenum, jejunum, or ileum. In various embodiments, the site in the gastrointestinal tract is cecum, colon, rectum, or anus. In various embodiments, the site in the gastrointestinal tract is ascending colon, transverse colon, descending colon, or sigmoid flexure.

Diseases or Conditions

In various embodiments, the disease or condition caused, at least in part, by having high methanogen quantities or associated with having high methanogen quantities include but are not limited obesity, constipation, fatty liver (NASH), pre-diabetes, diabetes, insulin resistance, glucose and intolerance.

In various embodiments, the disease or condition caused, at least in part, by having low methanogen quantities or associated with having low methanogen quantities include but are not limited Crohn's disease or ulcerative colitis.

Therapies for Selection or Treatment of a Disease or Condition when Methanogen Quantity is High Therapies that directly inhibit the growth of methanogens and thereby treat disease or conditions caused by or related to high methanogen quantity, or reduce the likelihood of having disease or conditions caused by or related to high methanogen quantity.

In various embodiments, once a high methanogen quantity is detected, these therapies can be administered alone or concurrently with a known therapy that treats the disease or condition as described herein.

In various embodiments an antibiotic or a combination of two or more antibiotics can be selected and/or administered to subjects who have methanogen quantity higher than the reference value. Examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole.

In various embodiments, the antibiotic selected and/or administered is rifaximin. The rifaximin therapy selected and/or administered can be 200-2400 mg/dose, administered two or three times per day. In various embodiments the dosage can be about 50, 75, 100, 125, 150, 175, 200, 250, 300, 350, 400, 450, 500, 550, 600, 650, or 700 mg/dose, In various embodiments, the rifaximin therapy can be administered one, two, three, four or five times a day. In various embodiments, the therapy can be administered for 5, 7, 10, 14, 15, 20, 21, or 28 days. In various embodiments, the therapy can be re-administered after a period of no therapy.

In various embodiments, the antibiotic selected and/or administered is neomycin. The neomycin therapy selected and/or administered can be 500-1000 mg/dose, administered two times per day. In various embodiments the dosage can be about 100, 200, 300, 400, 500, 600, 700, 750, 1000, 1100, 1200, 1300, 1400, or 1500 mg/dose. In various embodiments, the neomycin therapy can be administered one, two, three, four or five times a day. In various embodiments, the therapy can be administered for 5, 7, 10, 14, 15, 20, 21, or 28 days. In various embodiments, the therapy can be re-administered after a period of no therapy.

In various embodiments, the antibiotic selected and/or administered is vancomycin. The vancomycin therapy selected and/or administered can be about 125 mg/dose, administered four times per day. In various embodiments the dosage can be about 50, 75, 100, 125, 150, 175, 200, 250, 300, 350, 400, 450, or 500 mg/dose, In various embodiments, the vancomycin can be administered one, two, three, four or five times a day. In various embodiments, the therapy can be administered for 5, 7, 10, 14, 15, 20, 21, or 28 days. In various embodiments, the therapy can be re-administered after a period of no therapy.

In various embodiments, the antibiotic selected and/or administered is metronidazole. The metronidazole therapy selected and/or administered can be 250-500 mg/dose, administered three times per day. In various embodiments the dosage can be about 50, 75, 100, 125, 150, 175, 200, 250, 300, 350, 400, 450, 500, 550, 600, 650, 700, 800, 900, or 1000 mg/dose, In various embodiments, the metronidazole therapy can be administered one, two, three, four or five times a day. In various embodiments, the therapy can be administered for 5, 7, 10, 14, 15, 20, 21, or 28 days. In various embodiments, the therapy can be re-administered after a period of no therapy.

In various embodiments, the two or more antibiotics selected and/or administered are rifaximin and neomycin. In various embodiments, the two or more antibiotics selected and/or administered are rifaximin and metronidazole.

Particularly effective antibiotics may be non-absorbable antibiotics. Examples of non-absorbable antibiotics include but are not limited to rifaximin, neomycin, Bacitracin, vancomycin, teicoplanin, ramoplanin, and paramomycin.

In some embodiments, a probiotic agent that inhibits the growth of methanogens, for example, *Bifidobacterium* sp. or *Lactobacillus* species or strains, e.g., *L. acidophilus, L. rhamnosus, L. plantarum, L. reuteri, L. paracasei* subsp. *paracasei*, or *L. casei* Shirota, or probiotic *Saccharomyces* species, e.g., *S. cerevisiae*, is selected and/or administered. The probiotic agent that inhibits the growth of methanogensis by typically administered in a pharmaceutically acceptable ingestible formulation, such as in a capsule, or for some subjects, consuming a food supplemented with the inoculum is effective, for example a milk, yoghurt, cheese, meat or other fermentable food preparation. These probiotic agents can inhibit the growth of methanogens, for example, by competing against methanogens for growth and thus reduce or inhibit the growth of methanogens.

In various embodiments, the therapy selected and/or administered can be a reduced-calorie diet. This can be particularly beneficial for subjects who are or are susceptible to being obese, or subjects who are or are susceptible to being pre-diabetic, diabetic, insulin resistant, and/or glucose intolerant.

In various embodiments, the therapy selected and/or administered can be a reduced-fat diet. The inventors' research suggests that methanogen growth increases in the presence of fat. Thus, a reduced-fat diet can inhibit the growth of methanogens and treat the diseases or conditions caused by or related to high methanogen levels, or reduce the likelihood of having these diseases or conditions.

In various embodiments, the therapy selected and/or administered can be an elemental diet. A comestible total enteral nutrition (TEN) formulation, which is also called an "elemental diet" are commercially available, for example, Vivonex® T.E.N. (Sandoz Nutrition, Minneapolis, Minn.) and its variants, or the like. A useful total enteral nutrition formulation satisfies all the subject's nutritional requirements, containing free amino acids, carbohydrates, lipids, and all essential vitamins and minerals, but in a form that is readily absorbable in the upper gastrointestinal tract, thus depriving or "starving" the methanogen of nutrients of at least some of the nutrients they previously used for proliferating. Thus, methanogen growth is inhibited.

In various embodiments, the therapy selected and/or administered can be a selective inhibitor of methanogenesis, such as monensin or a statin (HMG-CoA reductase inhibitor). Statins can selectively inhibit the growth of methanogens without significantly inhibiting the growth of non-methanogens. Examples of statins include but are not limited to atorvastatin, fluvastatin, lovastatin, pitavastatin, pravastatin, rosuvastatin, and simvastatin.

Therapies that can be Selected and/or Administered that Treats Disease or Conditions Caused by or Related to High Methanogen Level In various embodiments, once a high methanogen quantity is detected, these therapies that treat the disease or condition can be administered alone or along with a therapy that directly inhibits the growth of methanogens, as described herein.

Dosages and treatment regimens can be as indicated by the manufacturer for the indicated disease or condition.

In various embodiments, the therapy selected and/or administered can be an anti-obesity drug. Examples of anti-obesity drugs include but are not limited to phentermine, phentermine/topiramate, xenical, lorcaserin, and rimonabant.

In various embodiments, the therapy selected and/or administered can be a drug or a combination drug to treat pre-diabetes, diabetes, insulin resistance, or glucose intolerance. Examples of drugs include but are not limited to alpha-glucosidase inhibitors, amylin analogs, dipeptidyl peptidase-4 inhibitors, GLP1 agonists, meglitinides, sulfonylureas, biguanides, thiazolidinediones (TZD), and insulin. Additional examples of drugs include bromocriptine and welchol. Examples of alpha-glucosidase inhibitors include but are not limited to acarbose and miglitol. An example of an amylin analog is pramlintide. Examples of dipeptidyl peptidase-4 inhibitors include but are not limited to Saxagliptin, Sitagliptin, Vildagliptin, Linagliptin, and Alogliptin. Examples of GLP1 agonist include but are not limited to liraglutide, exenatide, exenatide extended release. Examples of meglitinide include but are not limited to nateglinide, and repaglinide. Examples of sulfonylurea include but are not limited to chlorpropamide, Glimepiride, Glipizide, Glyburide, Tolazamide, and Tolbutamide. Examples of biguanide include but are not limited to Metformin, Riomet, Glucophage, Glucophage XR, Glumetza. Examples of thiazolidinedione include but are not limited to Rosiglitazone and Pioglitazone. Examples of insulin include but are not limited to Aspart, Detemir, Glargine, Glulisine, and Lispro. Examples of combination drugs include but are not limited to Glipizide/Metformin, Glyburide/Metformin, Pioglitazone/Glimepiride, Pioglitazone/Metformin, Repaglinide/Metformin, Rosiglitazone/Glimepiride, Rosiglitazone/Metformin, Saxagliptin/Metformin, Sitagliptin/Simvastatin, Sitagliptin/Metformin, Linagliptin/Metformin, Alogliptin/Metformin, and Alogliptin/Pioglitazone.

In various embodiments, the therapy selected and/or administered is to treat constipation. Examples of such therapies include, but are not limited to laxatives, diet, guanylate cyclase C agonists, and serotonin agonists. An example of guanylate cyclase C agonist is linaclotide. Examples of serotonin agonists include prucalorpride and tegaserod.

In various embodiments, the therapy selected and/or administered is to treat fatty liver. An example of such therapy is metformin.

Therapies that can be Selected and/or Administered to Directly or Indirectly Treat Diseases and Conditions Caused by or Related to Low Methanogen Quantity or No Detectable Methanogens In various embodiments, once a low methanogen quantity is detected or no detectable methanogens is determined, these therapies that directly promote the growth of methanogens or directly provides for colonization of methanogens, can be administered alone or concurrently with known therapies that treat these diseases or condition.

In various embodiments, the therapy selected and/or administered is to treat Crohn's disease and/or ulcerative colitis. An example of such therapy is administering a methanogen. In various embodiments, the methanogen is from the genus *Methanobrevibacter*. In Examples of *Methanobrevibacter* include but are not limited to *M. acididurans*,

*M. arboriphilus, M. curvatus, M. cuticularis, M. filiformis, M. gottschalkii, M. millerae, M. olleyae, M. oralis, M. ruminantium, M. smithii, M. thaueri, M. woesei,* and *M. wolinii.* In certain embodiments, the *Methanobrevibacter* is *Methanobrevibacter smithii* (*M. Smithii*).

Pharmaceutical Compositions and Routes of Administration

In various embodiments, the present invention provides pharmaceutical compositions including a pharmaceutically acceptable excipient along with a therapeutically effective amount of a therapeutic agent described herein.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In certain embodiments, the therapeutic agents of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals such as sodium, lithium, potassium, calcium, magnesium and the like, as well as nontoxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "pharmaceutically acceptable esters" refers to the relatively nontoxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs" are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use.

The term "prodrug" refers to compounds that are rapidly transformed in vivo to yield the functionally active one or more peptides or drugs as disclosed herein or a mutant, variant, analog or derivative thereof. A thorough discussion is provided in T. Higachi and V. Stella, "Pro-drugs as Novel Delivery Systems," Vol. 14 of the A. C. S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. A prodrug of the one or more peptides as disclosed herein or a mutant, variant, analog or derivative thereof can be designed to alter the metabolic stability or the transport characteristics of one or more peptides or drugs as disclosed herein or a mutant, variant, analog or derivative thereof, to mask side effects or toxicity, to improve the flavor of a compound or to alter other characteristics or properties of a compound. By virtue of knowledge of pharmacodynamic processes and drug metabolism in vivo, once a pharmaceutically active form of the one or more peptides or drugs as disclosed herein or a mutant, variant, analog or derivative thereof, those of skill in the pharmaceutical art generally can design prodrugs of the compound (see, e.g., Nogrady (1985) Medicinal Chemistry A Biochemical Approach, Oxford University Press, N.Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral.

"Transdermal" administration may be accomplished using a topical cream or ointment or by means of a transdermal patch.

"Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Compositions for parenteral use may be provided in unit dosage forms (e.g., in single-dose ampoules), or in vials containing several doses and in which a suitable preservative may be added (see below).

The composition may be in form of a solution, a suspension, an emulsion, an infusion device, or a delivery device for implantation, or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection.

Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

Via the ocular route, they may be in the form of eye drops.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins Pa., USA) (2000).

Typical dosages of a therapeutically effective amount of the therapeutic agent can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage can depend upon the judgment of the physician, the condition of the patient, and the effectiveness of the therapeutic method based.

Measuring Methanogens or Methanogen Syntrophic Microorganisms

In various embodiments, amplification-based assays can be used to measure the methanogen quantity or the quantity of methanogen syntrophic microorganisms. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy samples, provides a measure of the methanogen quantity.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

In still other embodiments of the methods provided herein, sequencing of individual nucleic molecules (or their amplification products) is performed. In one embodiment, a high throughput parallel sequencing technique that isolates single nucleic acid molecules of a population of nucleic acid molecules prior to sequencing may be used. Such strategies may use so-called "next generation sequencing systems" including, without limitation, sequencing machines and/or strategies well known in the art, such as those developed by Illumina/Solexa (the Genome Analyzer; Bennett et al. (2005) Pharmacogenomics, 6:373-20 382), by Applied Biosystems, Inc. (the SOLiD Sequencer; solid.appliedbiosystems.com), by Roche (e.g., the 454 GS FLX sequencer; Margulies et al. (2005) Nature, 437:376-380; U.S. Pat. Nos. 6,274,320; 6,258,568; 6,210,891), by Heliscope™ system from Helicos Biosciences (see, e.g., U.S. Patent App. Pub. No. 2007/0070349), and by others. Other sequencing strategies such as stochastic sequencing (e.g., as developed by Oxford Nanopore) may also be used, e.g., as described in International Application No. PCT/GB2009/001690 (pub. no. WO/2010/004273).

In still other embodiments of the methods provided herein, deep sequencing can be used to identify and quantify the methanogen or methanogen syntrophic microorganism. These techniques are known in the art.

Nucleic Acid Sample Preparation

A. Nucleic Acid Isolation

Nucleic acid samples derived from the biological sample from a subject that can be used in the methods of the invention to determine the methanogen quantity can be prepared by means well known in the art. For example, surgical procedures or needle biopsy aspiration can be used to biological samples from a subject.

In one embodiment, the nucleic acid samples used to compute a reference value are taken from at least 1, 2, 5, 10, 20, 30, 40, 50, 100, or 200 different organisms of that species. According to certain aspects of the invention, nucleic acid "derived from" genomic DNA, as used in the methods of the invention can be fragments of genomic nucleic acid generated by restriction enzyme digestion and/or ligation to other nucleic acid, and/or amplification products of genomic nucleic acids, or pre-messenger RNA (pre-mRNA), amplification products of pre-mRNA, or genomic DNA fragments grown up in cloning vectors generated, e.g., by "shotgun" cloning methods. In certain embodiments, genomic nucleic acid samples are digested with restriction enzymes.

B. Amplification of Nucleic Acids

Though the nucleic acid sample need not comprise amplified nucleic acid, in some embodiments, the isolated nucleic acids can be processed in manners requiring and/or taking advantage of amplification. The genomic DNA samples of the biological sample from a subject optionally can be fragmented using restriction endonucleases and/or amplified prior to determining analysis. In one embodiment, the DNA fragments are amplified using polymerase chain reaction (PCR). Methods for practicing PCR are well known to those of skill in the art. One advantage of PCR is that small quantities of DNA can be used. For example, genomic DNA from the biological sample from a subject may be about 150 ng, 175, ng, 200 ng, 225 ng, 250 ng, 275 ng, or 300 ng of DNA.

In certain embodiments of the methods of the invention, the nucleic acid from a biological sample of a subject is amplified using a single primer pair. For example, genomic DNA samples can be digested with restriction endonucleases to generate fragments of genomic DNA that are then ligated to an adaptor DNA sequence which the primer pair recognizes. In other embodiments of the methods of the invention, the nucleic acid from a biological sample of a subject is amplified using sets of primer pairs specific to methanogens. Such sets of primer pairs each recognize genomic DNA sequences flanking the gene wherein the methanogen detection or quantification is also to be assessed. A DNA sample suitable for hybridization can be obtained, e.g., by polymerase chain reaction (PCR) amplification of genomic DNA, fragments of genomic DNA, fragments of genomic DNA ligated to adaptor sequences or cloned sequences. Computer programs that are well known in the art can be used in the design of primers with the desired specificity and optimal amplification properties, such as Oligo version 5.0 (National Biosciences). PCR methods are well known in the art, and are described, for example, in Innis et al., eds., 1990, PCR Protocols: A Guide to Methods And Applications, Academic Press Inc., San Diego, Calif. It will be apparent to one skilled in the art that controlled robotic systems are useful for isolating and amplifying nucleic acids and can be used.

In other embodiments, where genomic DNA of a biological sample from a subject is fragmented using restriction endonucleases and amplified prior to analysis, the amplification can comprise cloning regions of genomic DNA of a biological sample from a subject. In such methods, amplification of the DNA regions is achieved through the cloning process. For example, expression vectors can be engineered to express large quantities of particular fragments of genomic DNA of a biological sample from a subject (Sambrook, J. et al., eds., 1989, Molecular Cloning: A Laboratory Manual, 2nd Ed., Cold Spring Harbor Laboratory Press, Cold Spring Harbor, N.Y., at pp. 9.47-9.51).

In yet other embodiments, where the DNA of a biological sample from a subject is fragmented using restriction endonucleases and amplified prior to analysis, the amplification comprises expressing a nucleic acid encoding a gene, or a gene and flanking genomic regions of nucleic acids, from the biological sample from the subject. RNA (pre-messenger RNA) that comprises the entire transcript including introns is then isolated and used in the methods of the invention to analyze and provide a methanogen quantity. In certain embodiments, no amplification is required. In such embodiments, the genomic DNA, or pre-RNA, from the a biological sample of a subject may be fragmented using restriction endonucleases or other methods. The resulting fragments may be hybridized to SNP probes. Typically, greater quantities of DNA are needed to be isolated in comparison to the quantity of DNA or pre-mRNA needed where fragments are amplified. For example, where the nucleic acid from a biological sample of a subject is not amplified, a DNA sample from a biological sample of a subject for use in hybridization may be about 400 ng, 500 ng, 600 ng, 700 ng, 800 ng, 900 ng, or 1000 ng of DNA or greater. Alternatively, in other embodiments, methods are used that require very small amounts of nucleic acids for analysis, such as less than 400 ng, 300 ng, 200 ng, 100 ng, 90 ng, 85 ng, 80 ng, 75 ng, 70 ng, 65 ng, 60 ng, 55 ng, 50 ng, or less, such as is used for molecular inversion probe (MIP) assays. These techniques are particularly useful for analyzing clinical samples, such as paraffin embedded formalin-fixed material or small core needle biopsies, characterized as being readily available but generally having reduced DNA quality (e.g., small, fragmented DNA) and/or not providing large amounts of nucleic acids.

C. Hybridization

The nucleic acid samples derived from a biological sample from a subject used in the methods of the invention can be hybridized to arrays comprising probes (e.g., oligonucleotide probes) in order to identify and/or quantify methanogens. In certain embodiments, the probes used in the methods of the invention comprise an array of probes that can be tiled on a DNA chip (e.g., SNP oligonucleotide probes). In some embodiments, the methanogen is determined by a method that does not comprise detecting a change in size of restriction enzyme-digested nucleic acid fragments. In other embodiments, SNPs are analyzed to identify or quantify the methanogen. Hybridization and wash conditions used in the methods of the invention are chosen so that the nucleic acid samples to be analyzed by the invention specifically bind or specifically hybridize to the complementary oligonucleotide sequences of the array, preferably to a specific array site, wherein its complementary DNA is located. In some embodiments, the complementary DNA can be completely matched or mismatched to some degree as used, for example, in Affymetrix oligonucleotide arrays such as those used to analyze SNPs in MIP assays. The single-stranded synthetic oligodeoxyribonucleic acid DNA probes of an array may need to be denatured prior to contact with the nucleic acid samples of a biological sample from a subject, e.g., to remove hairpins or dimers which form due to self-complementary sequences.

Optimal hybridization conditions will depend on the length of the probes and type of nucleic acid samples from a biological sample from a subject. General parameters for specific (i.e., stringent) hybridization conditions for nucleic acids are described in Sambrook, J. et al., eds., 1989, Molecular Cloning: A Laboratory Manual, 2nd Ed., Cold Spring Harbor Laboratory Press, Cold Spring Harbor, N.Y., at pp. 9.47-9.51 and 11.55-11.61; Ausubel et al., eds., 1989, Current Protocols in Molecules Biology, Vol. 1, Green Publishing Associates, Inc., John Wiley & Sons, Inc., New York, at pp. 2.10.1-2.10.16. Exemplary useful hybridization conditions are provided in, e.g., Tijessen, 1993, Hybridization with Nucleic Acid Probes, Elsevier Science Publishers B. V. and Kricka, 1992, Nonisotopic DNA Probe Techniques, Academic Press, San Diego, Calif.

D. Oligonucleotide Nucleic Acid Arrays

In some embodiments of the methods of the present invention, DNA arrays can be used to assess methanogen quantity that comprise complementary sequences. Hybridization can be used to determine the presence and/or quantity of methanogens. Various formats of DNA arrays that employ oligonucleotide "probes," (i.e., nucleic acid molecules having defined sequences) are well known to those of skill in the art. Typically, a set of nucleic acid probes, each of which has a defined sequence, is immobilized on a solid support in such a manner that each different probe is immobilized to a predetermined region. In certain embodiments, the set of probes forms an array of positionally-addressable binding (e.g., hybridization) sites on a support. Each of such binding sites comprises a plurality of oligonucleotide molecules of a probe bound to the predetermined region on the support. More specifically, each probe of the array is preferably located at a known, predetermined position on the solid support such that the identity (i.e., the sequence) of each probe can be determined from its position on the array (i.e., on the support or surface). Microarrays can be made in a number of ways, of which several are described herein. However produced, microarrays share certain characteristics, they are reproducible, allowing multiple copies of a given array to be produced and easily compared with each other.

In certain embodiments, the microarrays are made from materials that are stable under binding (e.g., nucleic acid hybridization) conditions. The microarrays are preferably small, e.g., between about 1 $cm^2$ and 25 $cm^2$, preferably about 1 to 3 $cm^2$. However, both larger and smaller arrays are also contemplated and may be preferable, e.g., for simultaneously evaluating a very large number of different probes. Oligonucleotide probes can be synthesized directly on a support to form the array. The probes can be attached to a solid support or surface, which may be made, e.g., from glass, plastic (e.g., polypropylene, nylon), polyacrylamide, nitrocellulose, gel, or other porous or nonporous material. The set of immobilized probes or the array of immobilized probes is contacted with a sample containing labeled nucleic acid species so that nucleic acids having sequences complementary to an immobilized probe hybridize or bind to the probe. After separation of, e.g., by washing off, any unbound material, the bound, labeled sequences are detected and measured. The measurement is typically conducted with computer assistance. Using DNA array assays, complex mixtures of labeled nucleic acids, e.g., nucleic acid fragments derived a restriction digestion of genomic DNA, can be analyzed.

In certain embodiments, high-density oligonucleotide arrays are used in the methods of the invention. These arrays containing thousands of oligonucleotides complementary to defined sequences, at defined locations on a surface can be synthesized in situ on the surface by, for example, photolithographic techniques (see, e.g., Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; 5,510,270; 5,445,934; 5,744,305; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, Biosensors And Bioelectronics 11:687-690; Blanchard, 1998, in Synthetic DNA Arrays in Genetic Engineering, Vol. 20, J. K. Setlow, Ed., Plenum Press, New York at pages 111-123). Another method for attaching the nucleic acids to a surface is by printing on glass plates, as is described generally by Schena et al. (1995, Science 270:467-470). Other methods for making microarrays, e.g., by masking (Maskos and Southern, 1992, Nucl. Acids. Res. 20:1679-1684), may also be used. When these methods are used, oligonucleotides (e.g., 15 to 60-mers) of known sequence are synthesized directly on a surface such as a derivatized glass slide. The array produced can be redundant, with several oligonucleotide molecules.

One exemplary means for generating the oligonucleotide probes of the DNA array is by synthesis of synthetic polynucleotides or oligonucleotides, e.g., using N-phosphonate or phosphoramidite chemistries (Froehler et al., 1986, Nucleic Acid Res. 14:5399-5407; McBride et al., 1983, Tetrahedron Lett. 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, Nature 363:566-568; U.S. Pat. No. 5,539,083). In alternative embodiments, the hybridization sites (i.e., the probes) are made from plasmid or phage clones of regions of genomic DNA corresponding to SNPs or the complement thereof. The size of the oligonucleotide probes used in the methods of the invention can be at least 10, 20, 25, 30, 35, 40, 45, or 50 nucleotides in length. It is well known in the art that although hybridization is selective for complementary sequences, other sequences which are not perfectly complementary may also hybridize to a given probe at some level. Thus, multiple oligonucleotide probes with slight variations can be used, to optimize hybridization of samples. To further optimize hybridization, hybridization stringency condition, e.g., the hybridization temperature and the salt concentrations, may be altered by methods that are well known in the art.

In certain embodiments, the high-density oligonucleotide arrays used in the methods of the invention comprise oligonucleotides corresponding to a methanogen.

E. Labeling

In some embodiments, the nucleic acids samples, fragments thereof, or fragments thereof used in the methods of the invention are detectably labeled. For example, the detectable label can be a fluorescent label, e.g., by incorporation of nucleotide analogues. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes.

Radioactive isotopes include that can be used in conjunction with the methods of the invention, but are not limited to, 32P and 14C. Fluorescent molecules suitable for the present invention include, but are not limited to, fluorescein and its derivatives, rhodamine and its derivatives, texas red, 5'carboxy-fluorescein ("FAM"), 2',7'-dimethoxy-4',5'-dichloro-6-carboxy-fluorescein ("JOE"), N,N,N',N'-tetramethyl-6-carboxy-rhodamine ("TAMRA"), 6-carboxy-X-rhodamine ("ROX"), HEX, TET, IRD40, and IRD41.

Fluorescent molecules which are suitable for use according to the invention further include: cyanine dyes, including but not limited to Cy2, Cy3, Cy3.5, CY5, Cy5.5, Cy7 and FLUORX; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold.

Two-color fluorescence labeling and detection schemes may also be used (Shena et al., 1995, Science 270:467-470). Use of two or more labels can be useful in detecting variations due to minor differences in experimental conditions (e.g., hybridization conditions). In some embodiments of the invention, at least 5, 10, 20, or 100 dyes of different colors can be used for labeling. Such labeling would also permit analysis of multiple samples simultaneously which is encompassed by the invention.

The labeled nucleic acid samples, fragments thereof, or fragments thereof ligated to adaptor regions that can be used in the methods of the invention are contacted to a plurality of oligonucleotide probes under conditions that allow sample nucleic acids having sequences complementary to the probes to hybridize thereto. Depending on the type of label used, the hybridization signals can be detected using methods well known to those of skill in the art including, but not limited to, X-Ray film, phosphor imager, or CCD camera. When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. (1996) *Genome Res.* 6, 639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al. (1996) *Genome Res.* 6, 639-645. Alternatively, a fiber-optic bundle can be used such as that described by Ferguson et al. (1996) *Nat. Biotech.* 14, 1681-1684. The resulting signals can then be analyzed to determine methanogen quantity, using computer software.

F. Algorithms for Analyzing Methanogen Quantity

Once the hybridization signal has been detected the resulting data can be analyzed using algorithms. In certain embodiments, the algorithm for quantitating methanogens is based on well-known methods.

G. Computer Implementation Systems and Methods

In certain embodiments, the methods of the invention implement a computer program to calculate methanogen quantity. For example, a computer program can be used to perform the algorithms described herein. A computer system can also store and manipulate data generated by the methods of the present invention which comprises a plurality of hybridization signal changes/profiles during approach to equilibrium in different hybridization measurements and which can be used by a computer system in implementing the methods of this invention. In certain embodiments, a computer system receives probe hybridization data; (ii) stores probe hybridization data; and (iii) compares probe hybridization data to determine the quantity of methanogen. Whether the quantity is higher or lower than the reference value is calculated. In some embodiments, a computer system (i) compares the methanogen quantity to a threshold value or reference value; and (ii) outputs an indication of whether said methanogen quantity is above or below a threshold or reference value, or the presence of a disease or condition based on said indication. In certain embodiments, such computer systems are also considered part of the present invention.

Numerous types of computer systems can be used to implement the analytic methods of this invention according to knowledge possessed by a skilled artisan in the bioinformatics and/or computer arts.

Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; CRLMM software described in Silver et al. (2007) *Cell* 128, 991-1002; Aroma Affymetrix software described in Richardson et al. (2006) *Cancer Cell* 9, 121-132. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.). In certain embodiments, the computer comprises a database for storage of hybridization signal profiles. Such stored profiles can be accessed and used to calculate a methanogen quantity.

Kits

The present invention is also directed to a kit for the determination, selection, and/or treatment of the disease or conditions described herein. The kit is an assemblage of materials or components, including at least one of the inventive compositions. Thus, in some embodiments the kit contains a composition including a therapeutic agent, as described above. In other embodiments, the kit contains primers for the quantification of methanogens or methanogen syntrophic microorganisms.

The exact nature of the components configured in the inventive kit depends on its intended purpose. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to quantify the methanogens or methanogen syntrophic microorganisms, or to inhibit the growth of methanogens or methanogen syntrophic microorganisms, or to treat disease or conditions caused by or associated with methanogens or methanogen syntrophic microorganisms Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Patient Inclusion and Exclusion Criteria

The study was approved by the inventors' institutional review board, and informed consent was obtained from all participants. Consecutive Rome II positive IBS subjects aged 18-65 years of age who presented for lactulose breath testing were eligible for the study. Patients were excluded if they had any of the following: a history of abdominal surgery such as bowel resection (except cholecystectomy or appendectomy), known intestinal disorder such as inflammatory bowel disease, abdominal adhesions, perirectal or intestinal fistula, unstable thyroid disease, diabetes, cancer, HIV, pregnancy, use of medications known to affect intestinal motility such as narcotics, imodium, and tegaserod, or antibiotic usage within the past 1 month.

Collection of Breath and Stool Samples

All patients were first asked to complete a bowel symptom questionnaire in order to determine the relative degree of constipation to diarrhea based on C-D VAS scoring as previously validated [13]. Subjects then underwent lactulose breath testing (LBT). As part of the LBT, subjects were asked to ingest 10 µm oral lactulose in solution (Pharmaceutical Associates, Inc., Greenville, S.C.) after a baseline breath sample. Lactulose is a polysaccharide that is not digested by humans, but can be utilized by enteric flora. Repeat breath samples were then obtained every 15 minutes after lactulose ingestion until 180 minutes, and levels of methane and hydrogen were analyzed using gas chromatography (Quintron instrument company, Milwaukee, Wis.). A positive methane breath test was defined as a breath methane level ≥3 ppm as previously published [5, 13]. Using the questionnaire and breath test results, subjects who had methane on breath analysis and constipation predominant IBS were selected. The control group included those with any form of IBS who did not test positive for methane on breath testing. After completion of breath testing, all subjects were provided a stool container and instructions on how to collect the stool sample. Patients returned the stool sample that was fresh frozen within 24 hours of collection.

Stool PCR Testing

From each stool sample, bacterial DNA was extracted using QIAamp PCR kit (Qiagen, Hilden, Germany). PCR (Eppendorf mastercycler gradient) with previously published universal 16S rDNA primer was used to detect the presence of total bacteria in stool. Quantitative-PCR was performed on the same stool samples using the rpoB gene primer specific forts. smithii only (Table 1). In addition, quantitative PCR was also conducted to determine total bacteria count using universal primers (Table 1).

TABLE 1

Various PCR primers used to detect bacterial DNA in stool

| Organism | Target | Primers (5'-3') | Amplicon Size | SEQ ID NO |
|---|---|---|---|---|
| Universal | 16S rDNA | TCCTACGGGAGGCAG CAGT | 466 bp | 1 |
| | | GGACTACCAGGGTAT CTAATCCTGTT | | 2 |
| M. Smithii | rpoB | AAGGGATTTGCACCC AACAC | 70 bp | 3 |
| | | GACCACAGTTAGGAC CCTCTGG | | 4 |

Quantitative PCR was performed with the CFX96' Real-Time PCR Detection System (Bio-Rad Laboratoies, Hercules, Calif.) using optical grade 96-well plates. Duplicate samples were routinely used for the determination of DNA by real-time PCR. The PCR reaction was performed in a total volume of 20 μl using the iQ SYBR GREEN Supermix (Bio-Rad laboratories), containing 300 nM each of the universal forward and reverse primers. The reaction conditions were set at 95° C. for 3 min followed by 40 cycles at 95° C. for 10 s, 55° C. for 10 s and 72° C. for 30 s then 95° C. for 10 s. Data analysis made use of CFX Manager software supplied by Bio-Rad. To generate standard curves for total bacteria, the Ct values were plotted relative to the template DNA extracted from corresponding serial tenfold dilution of cultures of Escherichia coli strain ATCC 25922. Escherichia coli strain ATCC 25922 was previously grown in TB Growth Media (MO BIO Laboratories, Inc. Carlsbad, Calif.) to a concentration of $10^8$ CFU then plated on LB (ISC BioExpress, Kaysville, Utah) agar plates to verify colony counts. The $10^8$ CFU Escherichia coli solution was subjected to DNA extraction by using a Qiaamp® DNA Mini kit (Qiagen). The extracted DNA was used to create ten-fold dilutions and establish a standard curve. Similarly, calibration curves for M. Smithii were made by aliquoting ten-fold dilutions of $10^8$ CFU M. Smithii liquid culture. Concentration was determined by measuring optical density at 600 nm.

Statistical Analysis

Mann Whitney U test was utilized for non-parametric data and student's t-test was used for normally distributed data. The quantity of M. smithii was compared to the amount of methane on breath testing using Spearman rank correlation. Comparing breath test parts per million between hydrogen and methane utilized Pearson regression analysis. In addition, M. smithii was represented as a ratio percent to the combined total bacteria and M. smithii counts and this percent was also compared to breath test status, methane levels and degree of constipation. All tests were two-tailed and statistical significance was defined as $P<0.05$.

Baseline Characteristics

A total of 9 patients (C-IBS with positive methane breath analysis) and 10 controls (IBS with no breath methane) met the inclusion criteria. The majority of subjects in each group were females (8 of 9 in methane group and 8 of 10 among the non-methane controls). The average age was no different between the two groups (43.8±8.7 years in methane positive vs. 41.9±9.9 years in methane negative subjects). The validated symptom C-D score (range of score from −100 to +100) was 51.1±37.8 mm in the C-IBS with methane group which was greater than −1.0±35.1 mm for non-methane subjects ($P<0.01$) indicating significant constipation in methane positive subjects relative to diarrhea. There was no difference in bloating or abdominal pain severity between the groups.

PCR Results from Stool

On q-PCR, M. smithii samples were not interpretable due to poor sample in 2 methane and 1 hydrogen producing subjects leaving 7 methane and 9 non-methane producing subjects eligible for analysis. In the case of q-PCR for total bacterial counts, 6 samples were not interpretable leaving 13 (6 breath methane positive and 7 breath methane negative) for analysis. In determining the percent M. smithii, there were 12 samples in which both M. smithii and bacterial levels were measured.

Examining M. smithii first, M. smithii was detected in both methane producers as well as non-methane subjects. However, the presence of M. smithii was significantly higher in breath methane positive subjects ($1.8×10^7±3.0×10^7$ copies per gm wet stool) as compared to those with negative breath methane ($3.2×10^5±7.6×10^5$ copies per gm wet stool) ($p<0.001$). Based on these findings, the minimum threshold of M. smithii in order to produce positive lactulose breath testing for methane was deemed to be $4.2×10^5$ copies per gm of wet stool (FIG. 1).

Figure 2:
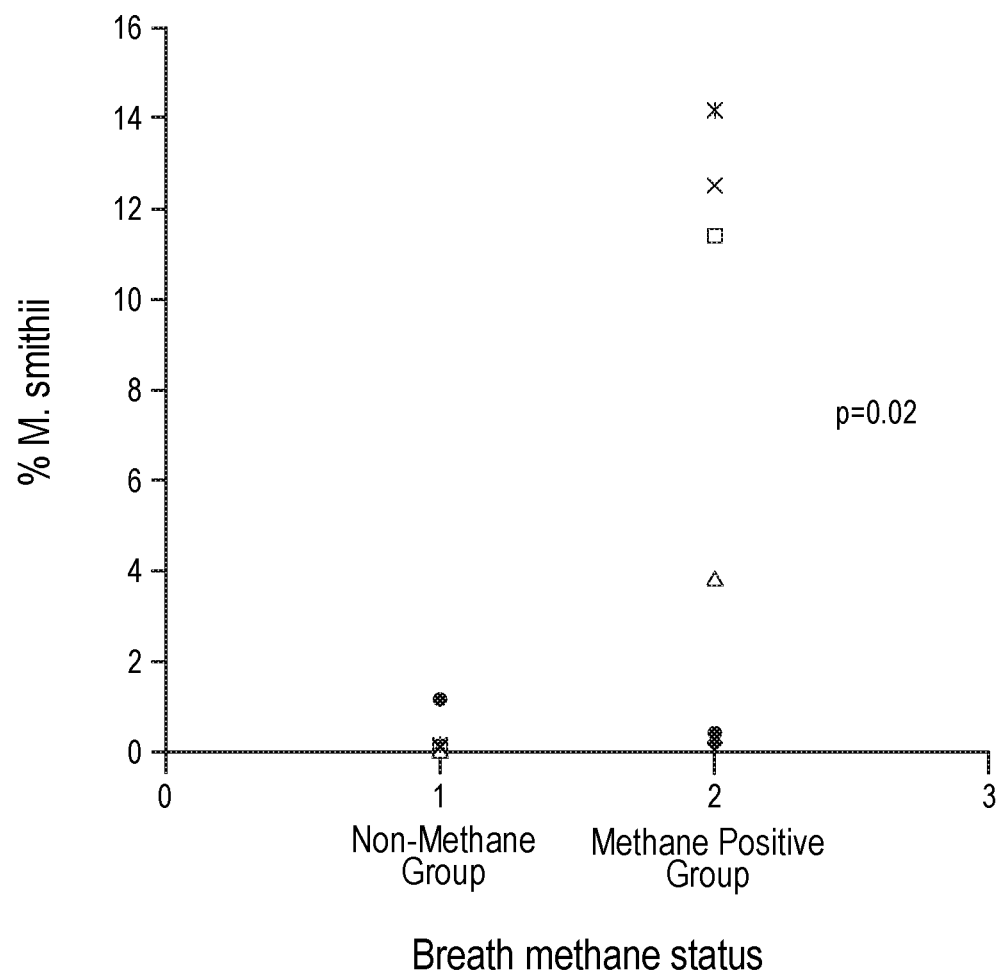
FIG. 2 depicts percent *M. smithii* relative to prokaryotic bacteria as determinant of detection of methane on breath in accordance with various embodiments of the present invention.

To further evaluate this relationship, the ratio of M. smithii to the combined total bacteria and M. smithii was expressed as a percent. In the non-methane producers, the percent M. smithii was 0.24±0.47% and among methane producing subjects was 7.1±6.3% ($P=0.02$) (FIG. 2). Based on percent counts, M. smithii greater than 1.2% was always indicative of positive breath methane.

Comparing M. smithii and Breath Methane and Hydrogen Levels on Breath Test

Figure 3:
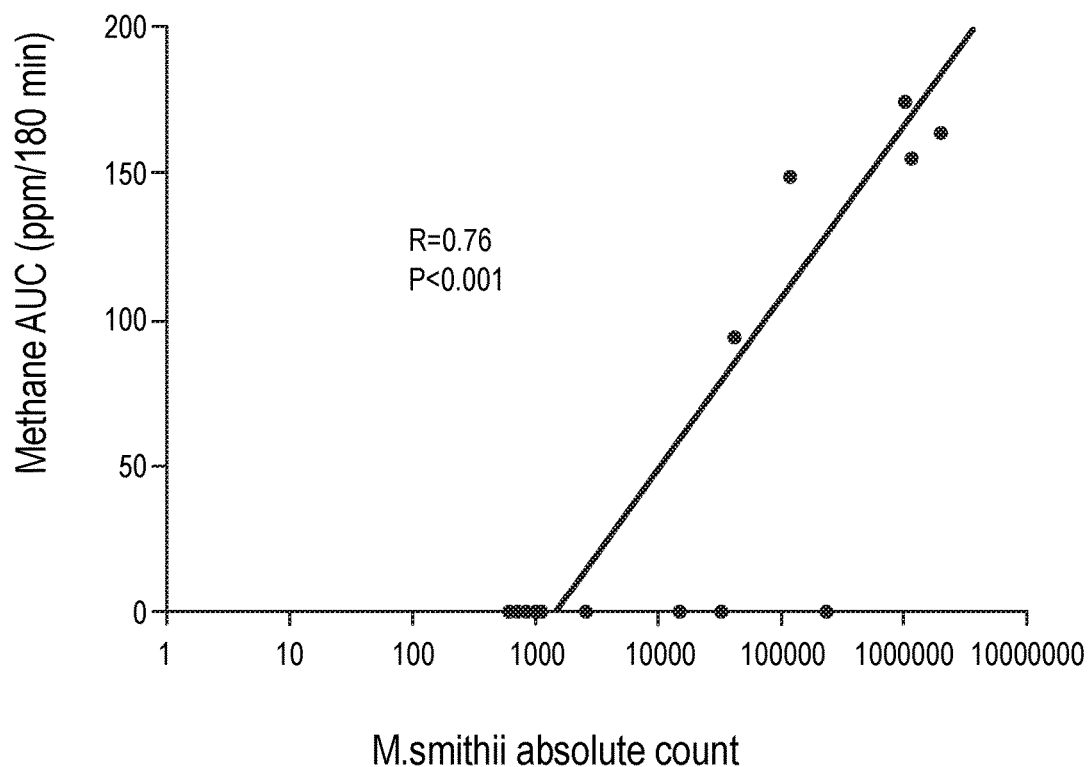
FIG. 3 depicts correlation between *M. smithii* and breath methane AUC in accordance with various embodiments of the present invention.
Figure 4:
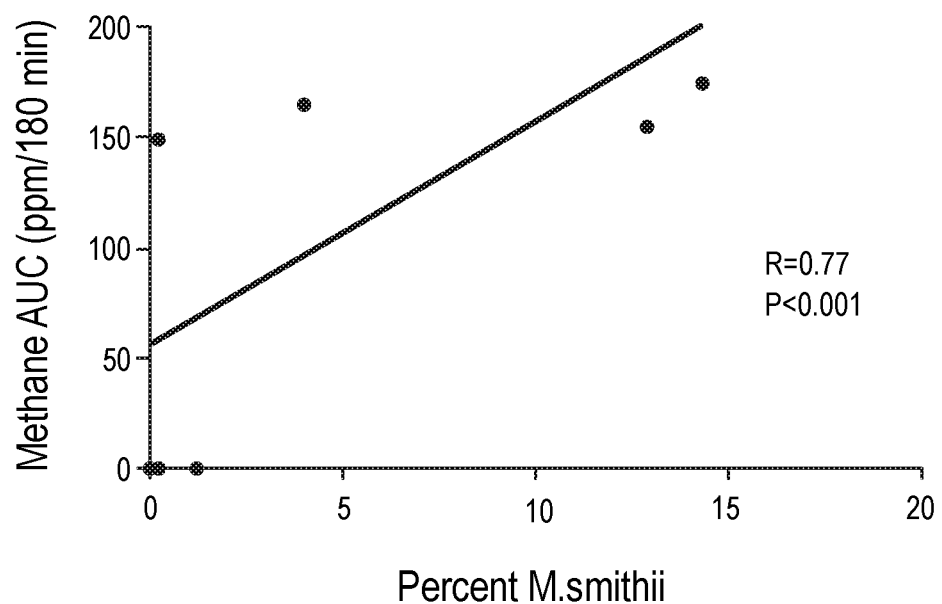
FIG. 4 depicts correlation between percent *M. smithii* to total prokaryotes and breath methane AUC in accordance with various embodiments of the present invention.

The amount of breath methane produced as determined by 180 min AUC correlated significantly with the quantity of M. smithii in stool ($R=0.76$, $P<0.001$) (FIG. 3). While total bacterial counts did not correlate with methane on breath testing, the percent M. smithii was highly correlated with the level of methane on breath test ($R=0.77$, $P=0.001$) (FIG. 4).

Figure 5:
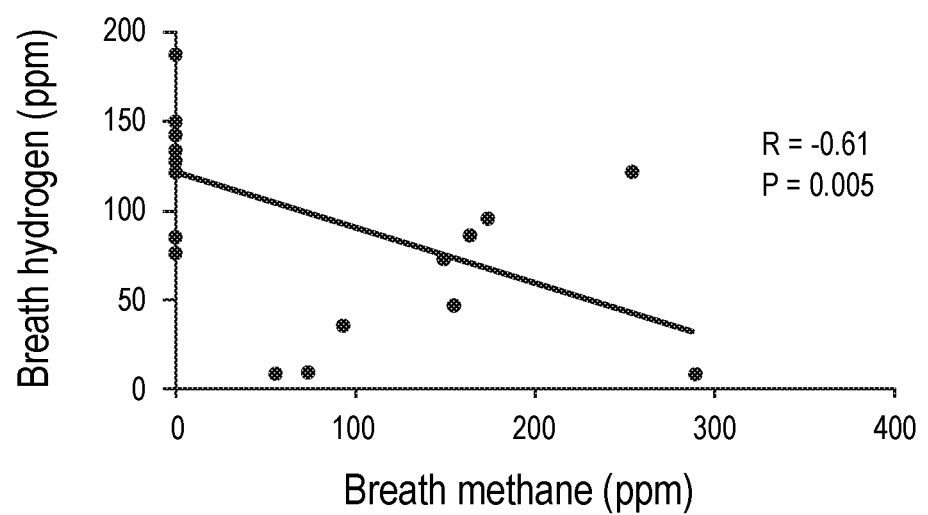
FIG. 5 depicts correlation between hydrogen and methane in breath AUC in accordance with various embodiments of the present invention.

In contrast to methane, when breath hydrogen was compared to quantities of M. smithii, total prokaryotic bacteria and the percent of M. smithii, no trend was seen. However, there was an expected hydrogen utilization by methane as suggested by an inverse correlation between breath methane AUC and hydrogen AUC ($R=−0.61$, $P=0.005$) (FIG. 5).

Constipation Symptoms, M. smithii and Total Bacterial Count

Figure 6:
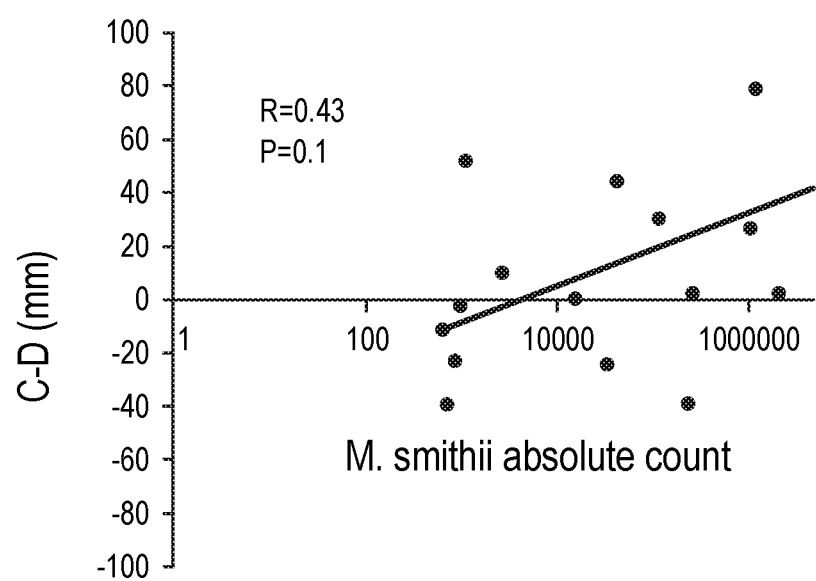
FIG. 6 depicts relationship between *M. smithii* level and the relative degree of constipation to diarrhea in accordance with various embodiments of the present invention. C-D is a validated measure of the relative degree of constipation to diarrhea. The larger the number the more constipation is relative to diarrhea.
Figure 7:
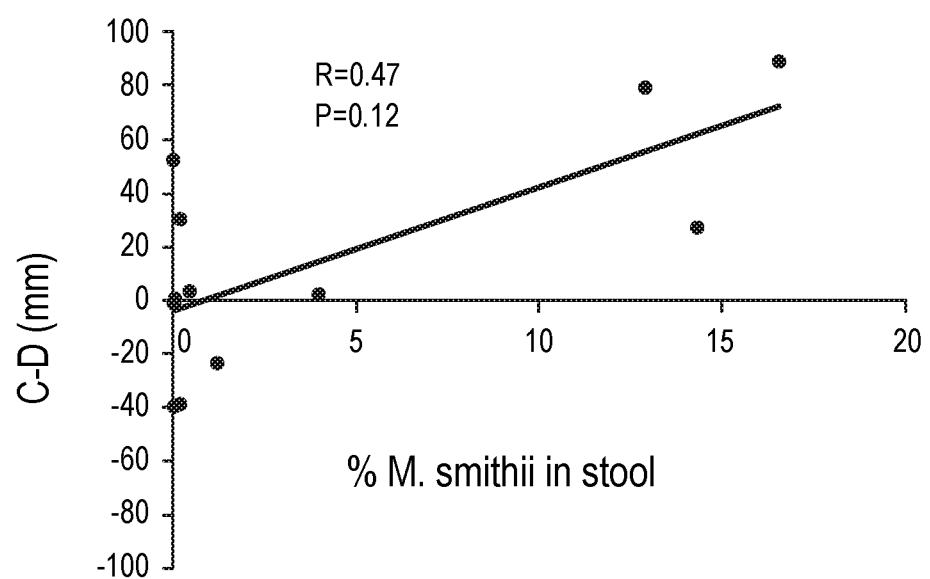
FIG. 7 depicts comparison of the percent *M. smithii* to total bacteria in the stool and relative degree of constipation in accordance with various embodiments of the present invention. C-D is a validated measure of the relative degree of constipation to diarrhea. The larger the number the more constipation is relative to diarrhea. The % *M. smithii* is determined by the amount of *M. smithii* relative to total prokaryotic bacteria.

Using the previously validated score examining constipation as a relative value to diarrhea (C-D), the inventors examined if M. smithii and total bacterial levels were predictive of constipation severity. Both absolute M. smithii (FIG. 6) ($R=0.43$, $P=0.1$) and percent M. smithii (FIG. 7) ($R=0.47$, $P=0.12$) did not quite meet significance in a comparison to the severity of constipation by C-D. Also in the case of M. smithii and percent M. smithii, no correlation was seen between levels and severity of abdominal pain or bloating.

Figure 8:
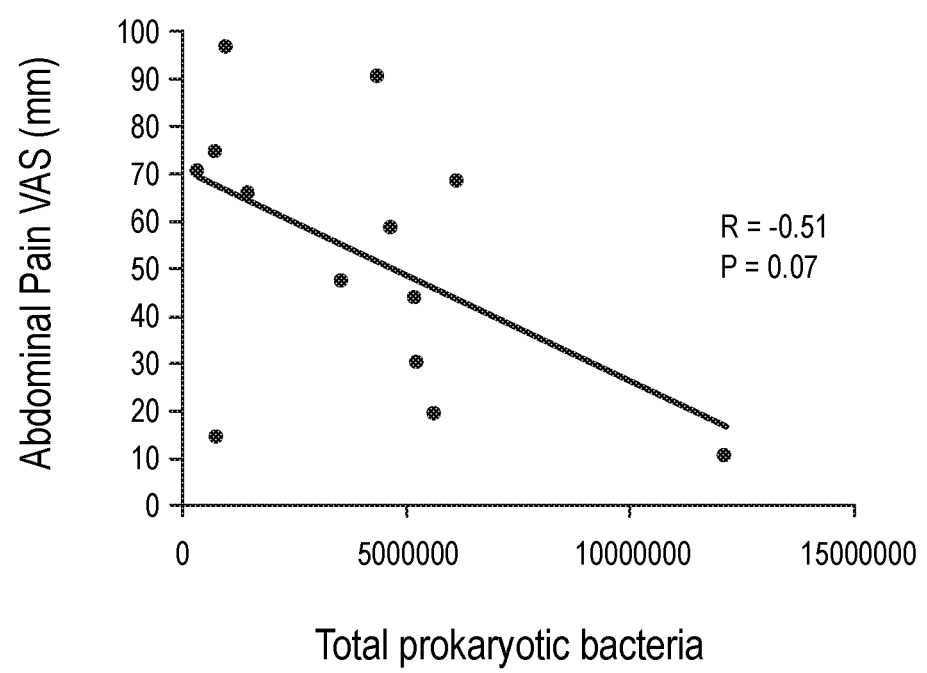
FIG. 8 depicts correlation between total prokaryote bacteria counts in stool and abdominal pain scores in accordance with various embodiments of the present invention.

In the case of total bacterial counts, there was no association with C-D score and no association with bloating. Although, there was an inverse correlation between bacterial levels and abdominal pain VAS scores ($R=−0.51$), it did not reach statistical significance ($P=0.07$) (FIG. 8).

Example 2

_M. smithii_ Hypercolonization of Rats

Twenty adult Sprague-Dawley rats were obtained as 21-day-old weanlings (Harlan Labs, Indianapolis, Ind.). After 3 days of quarantine, all rats were weighed, and then received a 1 ml aliquot of 5% sodium bicarbonate by oral gavage using a ball-tipped inoculating needle, in order to neutralize the gastric acid. After ~20 min, one group of rats (n=10) received a 0.5 ml gavage of _M. smithii_ in liquid growth media. A second group of rats (n=10) received a 0.5 ml gavage of liquid growth media. After another 20 min, rats gavaged with _M. smithii_ were given 0.2 ml enemas of the same inoculate following isoflurane anesthesia in a dessicator jar. The gavage and enemas were performed to determine whether _M. smithii_ levels in intestine could be enhanced through hypercolonization.

Tracking Colonization by _M. smithii_

After inoculation, all rats were housed two per microisolater cage under standard vivarium procedures and maintained on normal rodent chow (5.7% fat) (Lab Rodent Diet 5001; Newco Distributors, Rancho Cucamonga, Calif.). Fresh stool samples were collected daily for the first week, and then approximately every 2 weeks thereafter.

The stool specimens on specific weeks were tested for the levels of _M. smithii_ and of total bacteria by performing qPCR as previously described (27). _M. smithii_ levels were quantitated using primers for the RpoB gene (5'-AAGGGATTTGCACCCAACAC-3' (forward) (SEQ ID NO:3) and 5'-GACCACAGTTAGGACCCTCTGG-3' (reverse) (SEQ ID NO:4)) and total bacteria were quantitated using 16S recombinant DNA (5'-TCCTACGGGAGGCAGCAGT-3' (forward) (SEQ ID NO:1) and 5'-GGACTACCAGGGTATCTAATCCTGTT-3' (reverse) (SEQ ID NO:2)). Animal weights were also obtained once a week.

Diet Manipulation

Rats were observed until three consecutive weights were obtained within 10 g to suggest an end of growth curve and arrival at adult weight (corresponded to day 112). On day 112, all rats were then switched to a high-fat diet (34.3% fat) (Teklad high fat diet TD.06414; Harlan Laboratories, Madison, Wis.) and maintained on this diet for 10 weeks until day 182. Fresh stool samples and animal weights were collected from all animals on a weekly basis. On day 182, all rats were returned to normal chow. Finally, on day 253, five rats from each group were again fed high-fat chow. The rats were maintained on their respective diets while stool samples and weekly weights continued to be obtained for 5 weeks until euthanasia at day 287. This last phase was to guarantee that 10 rats were on high-fat and 10 on normal chow for a period of time before euthanasia.

Euthanasia and Bowel Sampling

On day 287 post-inoculation, all rats were euthanized by CO2 asphyxiation and pneumothorax. Laparotomy was performed and sections of the left colon, cecum, ileum, jejunum, and duodenum were resected from each rat as previously described (A27). DNA was extracted from luminal contents of each segment as previously described (A27), and qPCR with _M. smithii_-specific and universal bacterial primers was performed to determine the levels of _M. smithii_ and total bacteria, respectively in each segment. The study protocol was approved by the Cedars-Sinai Institutional Animal Care Utilization Committee (IACUC).

Statistical Analysis

The levels of _M. smithii_ in stool by qPCR between inoculated and noninoculated rats were compared by Mann-Whitney U-test. Comparisons of body weight before and after diet changes were compared by paired t-test. Levels of _M. smithii_ in bowel segments or stool between groups were again compared by Mann-Whitney U-test. For comparison of _M. smithii_ levels before and after an intervention, Wilcoxon signed-rank test was used. For weights, data were expressed as mean±s.d. and data for _M. smithii_ levels were expressed as mean±s.e. Statistical significance was determined by $P<0.05$.

Colonization of Rats with _M. smithii_

Figure 9:
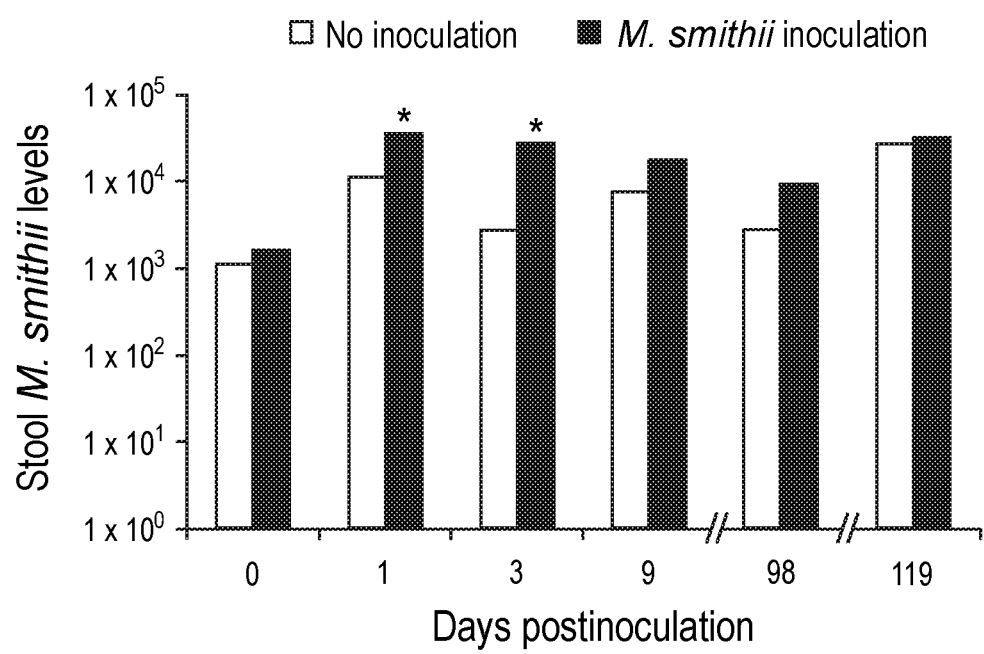
FIG. 9 depicts the effect of *Methanobrevibacter smithii* gavage on stool quantity of this species over time (before diet manipulation). *P<0.01. in accordance with various embodiments of the present invention.

At baseline, all rats demonstrated the presence of _M. smithii_ in the stool which were not different between groups (FIG. 9).

After inoculation with _M. smithii_, rats demonstrated an increased detection of stool _M. smithii_ than control animals. However, this did not persist as levels returned to control levels by day 9 (FIG. 9). Since hypercolonization did not occur, in the remaining experiments all of the rats were examined as a single group.

_M. smithii_ Levels and Weight after Initial Transition to High-Fat Diet

Figure 10:
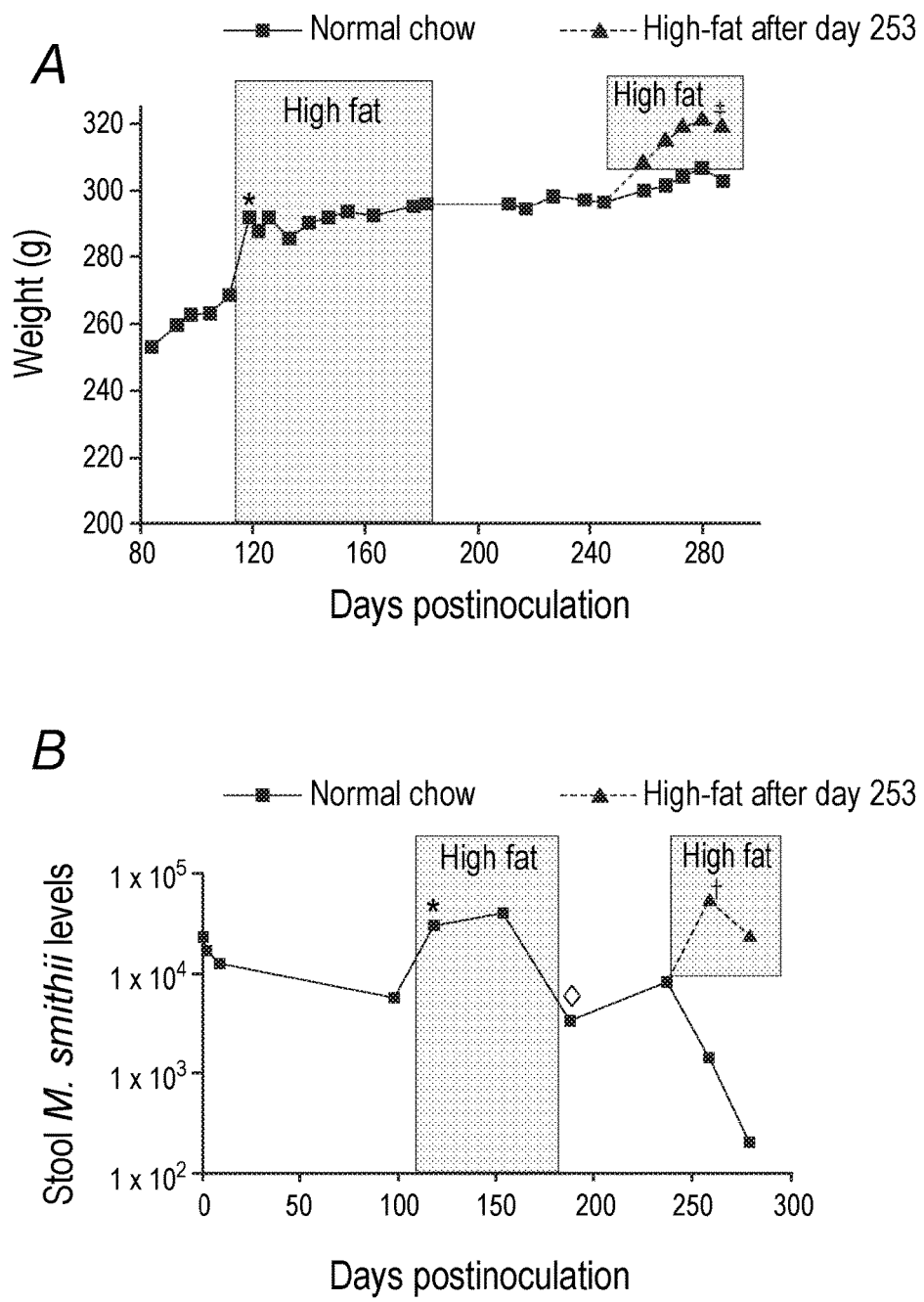
FIG. 10 depicts the effects of dietary fat content on rat weights and stool *Methanobrevibacter smithii* levels in accordance with various embodiments of the present invention. (A) Rat weights over time starting from the adult weight plateau. *P<0.00001 change in weight after 1 week on high-fat diet. ‡P<0.001 change in weight after return to highfat diet. (B) *Methanobrevibacter smithii* levels over time. *P<0.01 for increase in stool *M. smithii* after starting on high-fat chow. ◇P<0.001 for decrease in stool *M. smithii* after return to normal chow. †P=0.039 for increase in stool *M. smithii* after return to high-fat chow.

All rats were initially fed normal rat chow until three consecutive weights were obtained within a 10 g plateau to suggest the rats had reached adult weight. This plateau occurred in the 2 weeks preceding day 112 (FIG. 10a). During three consecutive measurements obtained between days 98 and 112, there was only a mean change in weight of 5.5±5.8 g. After switching to high-fat chow on day 112, a sudden increase in rat weights was observed (FIG. 10a). The average weight increased from 268±13 g on day 112 to 292±16 g on day 119 ($P<0.00001$). This resulted in a 1-week increase in weight of 23.2±9.5 g from day 112 to 119, as compared to 5.1±5.4 g in the preceding week ($P<0.00001$). Despite continuing on this high-fat diet, by day 182 the rats weighed 296±22 g, which was not statistically different from their weights 1 week after starting on high-fat chow ($P=0.39$).

Figure 11:
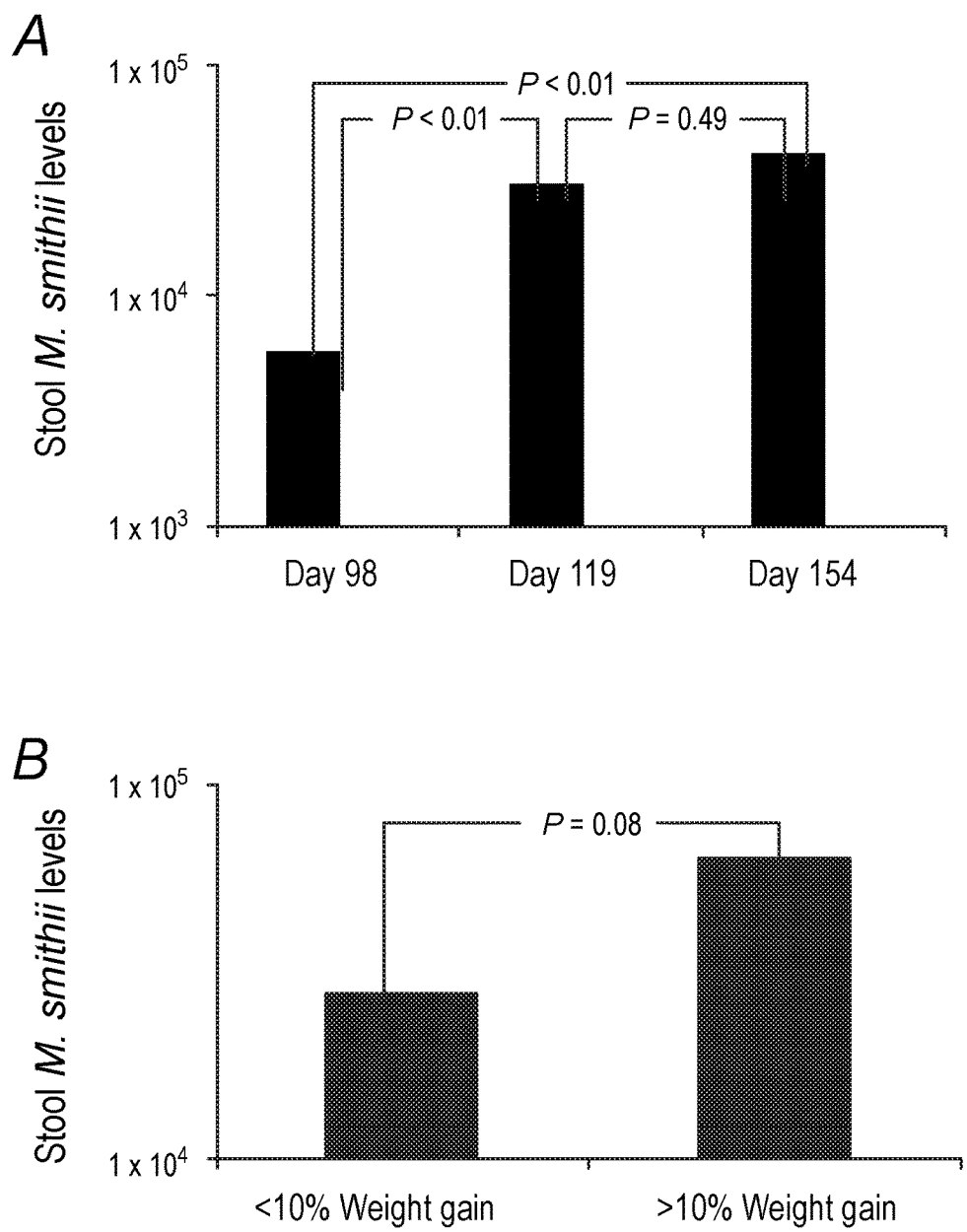
FIG. 11 depicts the effect of high-fat diet on stool *Methanobrevibacter smithii* levels in accordance with various embodiments of the present invention. (A)*Methanobrevibacter smithii* levels before, 1 week after, and 5 weeks after high-fat diet. (B) Stool *M. smithii* levels and the degree of weight gain. Comparing weight gain from day 98 to day 154. (C) Effect of returning to high-fat chow on stool *M. smithii* levels.
Figure 11:
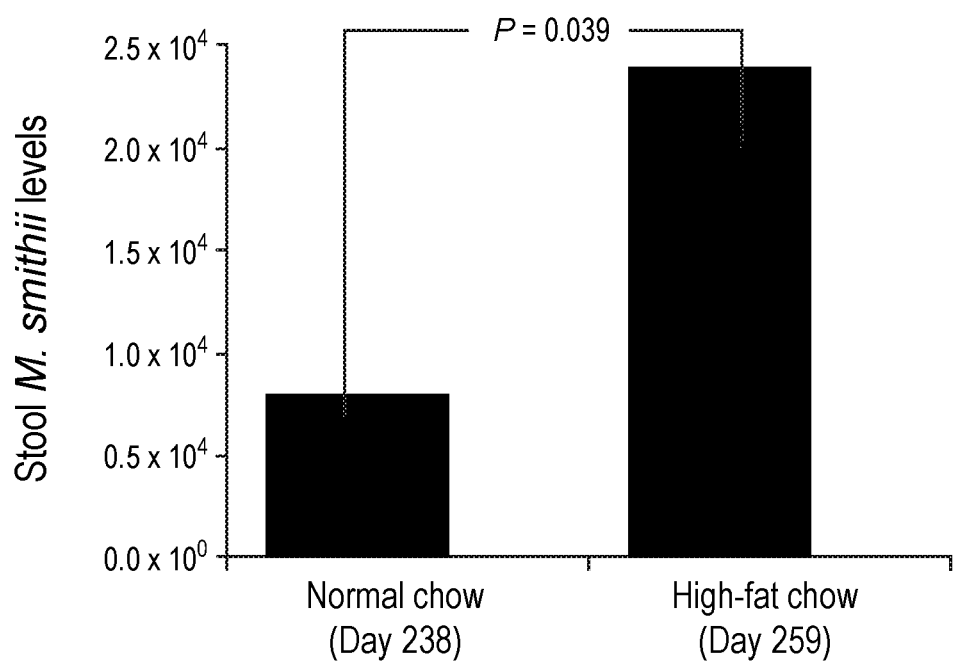

In addition to the weight change seen after switching to high-fat chow, stool _M. smithii_ levels also increased suddenly after the high-fat diet was implemented (FIG. 10b). _M. smithii_ levels were $5.6 \times 10^4 \pm 2.8 \times 10^3$ cfu/ml which increased by nearly 1 log to $3.0 \times 10^5 \pm 7.0 \times 10^3$ cfu/ml after 1 week of high-fat diet ($P<0.01$) (FIG. 11a). Like the change in body weight, the change in _M. smithii_ occurred in 1 week and did not further increase with additional weeks on high-fat chow (FIG. 11a).

In another analysis, rats were divided into groups based on those that gained more or less weight with high-fat. In another analysis, rats were divided into groups based on those that gained more or less weight with high-fat. In this analysis, rats which had >10% weight gain with high-fat had higher stool levels of _M. smithii_ than rats which gained less weight (<10% weight gain) ($P=0.08$, FIG. 11b).

_M. smithii_ and Body Weight on Returning to Normal Diet

On returning to normal chow after 10 weeks of high-fat diet on day 182, rats did not experience a reduction in body weight (FIG. 10a). As depicted in this figure, the rat weights remained at a plateau. However, the return to normal chow resulted in a gradual reduction in stool _M. smithii_ levels over time (FIG. 10b). On day 189, 1 week after cessation of fat and resumption of normal chow, _M. smithii_ levels were $3.4 \times 10^3 \pm 8.1 \times 10^2$ cfu/ml, which was significantly reduced from day 154 ($P<0.001$) (FIG. 10b). Stool _M. smithii_ levels continued to decline in rats continued on normal chow to the end of the study ($2.0 \times 10^2 \pm 2.0 \times 10^2$ cfu/ml) ($P<0.05$) (FIG. 10b).

Randomizing Back to High-Fat Diet a Second Time

In the final phase of the study, rats were randomized into two groups (10 rats returned to high-fat chow and the other 10 continued on normal chow). While FIG. 10a suggests that returning to high-fat chow did further increase body weight compared to continuing on normal chow, the differences in weights between the two groups (high-fat vs. normal chow) did not reach statistical significance for any timepoint. However, the 10 rats returned to high-fat chow exhibited an increase in average weight from 292±16 g to 319±26 g, which was significant (P<0.001, FIG. 10a). The return to high-fat chow also resulted in an increase in *M. smithii* levels in these animals (P=0.039, FIG. 11c).

Bacteria and *M. smithii* Levels by Bowel Segment Post-Mortem

Figure 12:
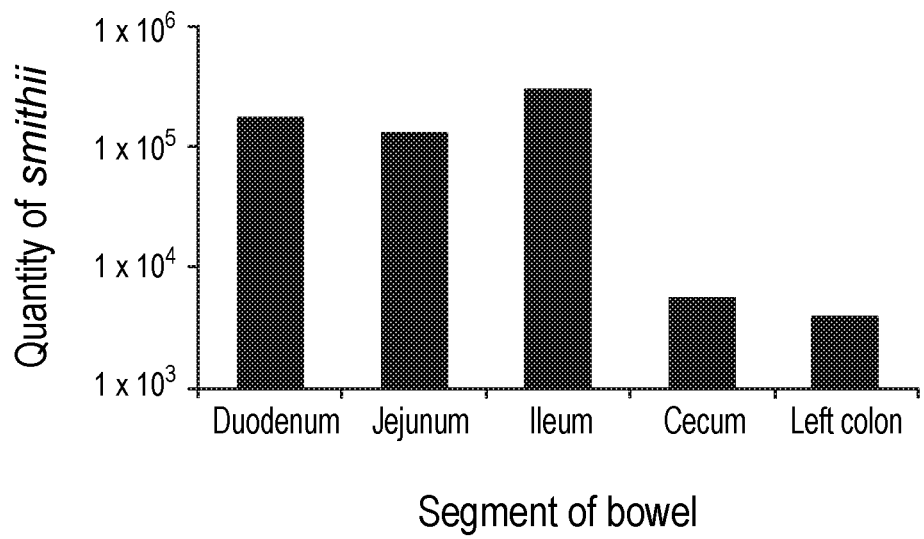
FIG. 12 depicts *Methanobrevibacter smithii* and total bacterial levels by segment of bowel in accordance with various embodiments of the present invention. (A) *Methanobrevibacter smithii* by segment of bowel post-mortem. P<0.001 between ileum and cecum and left colon; P=0.03 comparing ileum to jejunum and P=0.07 comparing ileum to duodenum. (B) Total bacteria by segment of bowel post-mortem.
Figure 12:
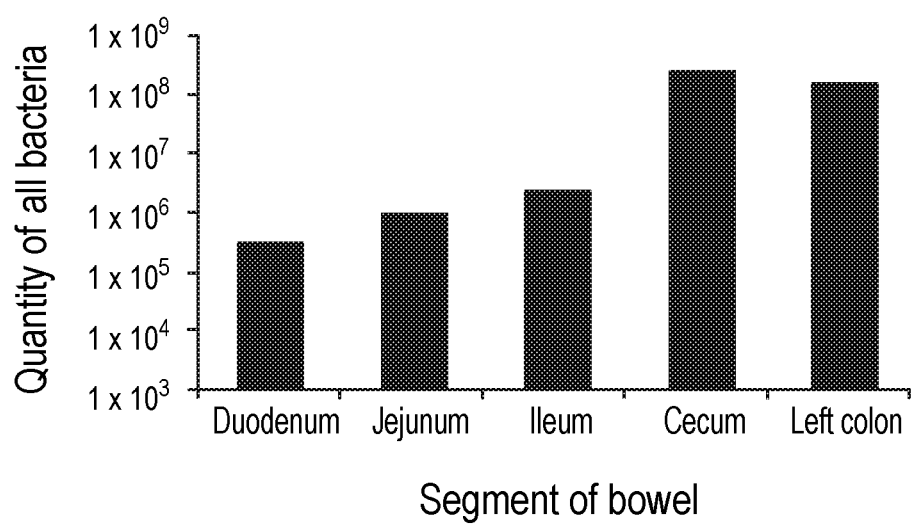
Figure 13:
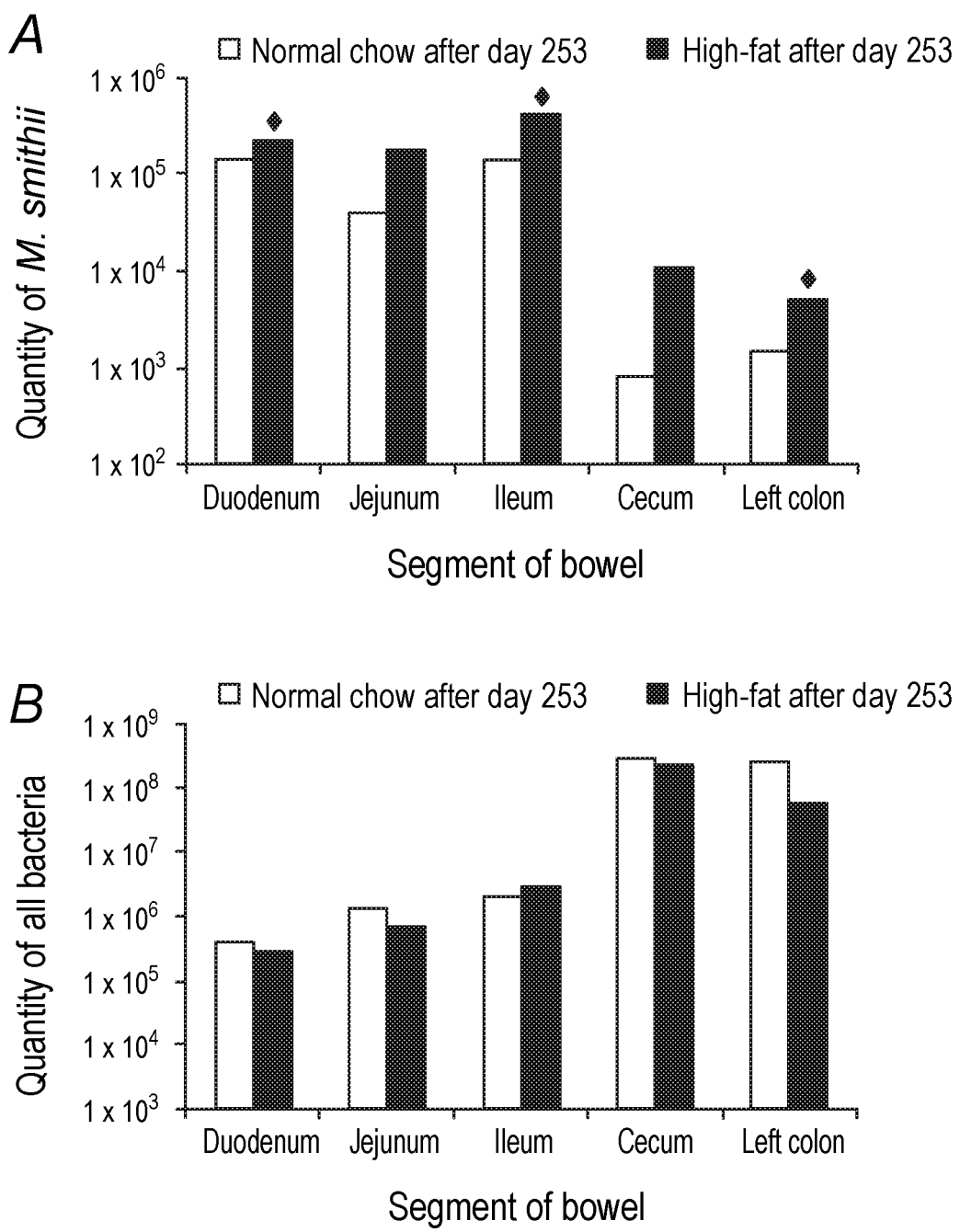
FIG. 13 depicts the effects of dietary fat content on *Methanobrevibacter smithii* and total bacterial levels in the bowel in accordance with various embodiments of the present invention. (A) *Methanobrevibacter smithii* throughout the bowel by diet. ♦P<0.05. (B) Total bacteria throughout bowel by diet. None of the comparisons were significant.

Following euthanasia on day 287 post-inoculation, sections of the left colon, cecum, ileum, jejunum, and duodenum were resected from each rat, and DNA was extracted from luminal contents of each segment. qPCR with *M. smithii*-specific and universal bacterial primers was used to determine the levels of *M. smithii* and total bacteria, respectively. Surprisingly, the highest levels of *M. smithii* were found in the small intestine, and were most elevated in the ileum (FIG. 12a). In contrast, total bacterial levels were lowest in the small intestine, and highest in the cecum and left colon (FIG. 12b). When the levels of *M. smithii* in each bowel segment were compared for rats switched to a high-fat diet in the final phase of the study vs. those maintained on normal chow, higher *M. smithii* levels were identified in all bowel segments of rats switched to a high-fat diet (FIG. 13a). However, only the duodenum, ileum, and cecum reached statistical significance. In contrast, no significant differences in total bacterial levels were identified between rats switched to a high-fat diet compared to those maintained on normal chow in any bowel segment (FIG. 13b).

Figure 14:
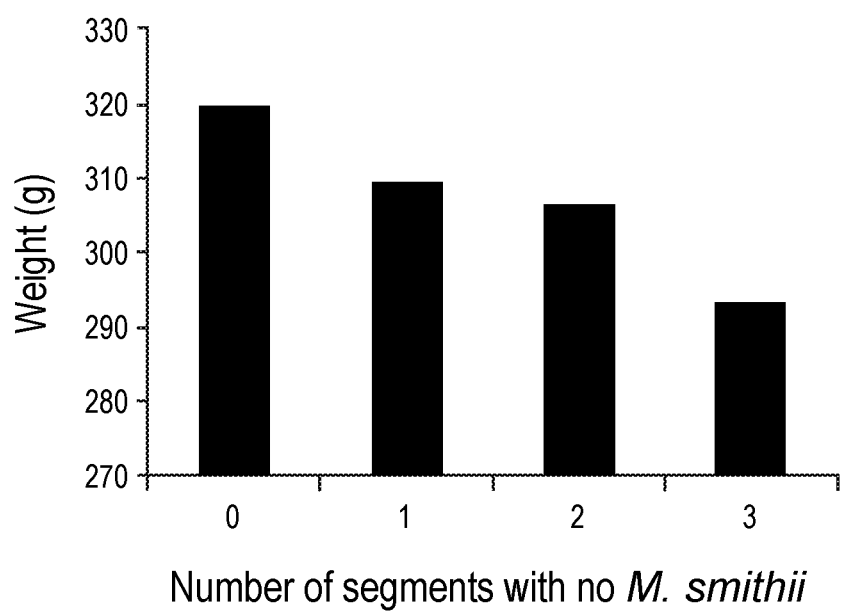
FIG. 14 depicts the number of segments with no *Methanobrevibacter smithii* colonization and weight in accordance with various embodiments of the present invention. Trend is not statistically significant.

Correlation Between Extent of Bowel Colonization with *M. smithii* and Weight in Rats The final comparison was to examine the distribution of *M. smithii* in the GI tract as a determinant of body weight. Although not statistically significant, rats with the greatest extent of *M. smithii* colonization (i.e., those with no uncolonized bowel segments) had higher weights than those with less widespread *M. smithii* colonization (i.e., those with one or more uncolonized bowel segments), irrespective of whether or not they were on high-fat chow in the final phase of the study (FIG. 14). The lowest body weight of all rats was recorded for a rat on high-fat chow that had three bowel segments out of five lacking *M. smithii* colonization.

Example 3

Study Population

Consecutive subjects presenting for lactulose breath testing were eligible for participation. Exclusion criteria were based on the ability to safely perform bioimpedance anthropometric measurements, and pregnant women and those with cardiac pacing/defibrillation devices were excluded. All subjects provided informed consent prior to participating in the study. The study was approved by Institutional Review Board at Cedars-Sinai Medical Center (Los Angeles, Calif.).

Questionnaire

Subjects completed a demographic and medical questionnaire and a bowel symptom questionnaire (B12) rating their last 7 days of intestinal complaints (bloating, diarrhea, constipation, and abdominal pain) on a visual analog scale from 0 to 100 mm, 100 being the most severe.

Lactulose Breath Test

Subjects presented to the medical center, having fasted for 12 hours as described previously (B13). Breath samples were collected in a dual-bag system (Quintron Instrument Co, Milwaukee, Wis.). After an initial breath collection, subjects ingested 10 g of lactulose syrup and then 250 mL of water. Breath samples were collected every 15 minutes for 2 hours and analyzed using the Breath-tracker-gas chromatograph (Quintron Instrument Co). Outputs included hydrogen, methane, and carbon dioxide. Hydrogen and methane were corrected for carbon dioxide to standardize to alveolar gas levels and reported in parts per million (ppm). Subjects with methane 3 ppm or greater were considered methane positive, as described previously (B13). Subjects with hydrogen greater than 20 ppm at or before 90 minutes during the test were considered hydrogen positive.

Anthropometrics

Bioimpedance testing was performed using the In-Body scale (Biospace Co, Ltd, Seoul, Korea), which has been validated in other studies (B12).BMI and percent body fat were determined based on height (measured via stadiometer) and electrical conductance.

Outcome Measures

Subjects were divided into 4 groups: normal (N) (<3 ppm methane and <20 ppm hydrogen at or before 90 minutes); hydrogen positive only (H+) (<3 ppm methane and hydrogen <20 ppm at or before 90 minutes); methane positive only (M+) (methane 3 ppm and hydrogen <20 ppm at or before 90 minutes); and methane and hydrogen positive (M+/H+) (methane 3 ppm and hydrogen 20 ppm at or before 90 minutes). Primary outcome measures were BMI and percent body fat, and primary analyses compared these measures across the 4 groups.

Data and Statistical Analysis

Age was compared across the groups by ANOVA and then Dunnett's post hoc test and gender by the Fisher exact test. Visual analog scale scores were compared across the groups by the Kruskal-Wallis test because of nonnormality. BMI and percent body fat were analyzed by analysis of covariance (ANCOVA) models. The initial ANCOVA models were 2-way factorial models (sex at 2 levels and group at 4 levels) with age as a covariate. Because the gender-by-group interaction was not significant (P=0.28 for BMI and P=0.37 for percent body fat), the interaction term was dropped in the ANCOVA model for each outcome. Age was significant and was retained in each model. Least squares (adjusted) means were used to compare the H+/M+ group with each of the other 3 groups. A 2-sided significance level of P=0.05 was used throughout. SAS version 9.2 (SAS Institute, Cary, N.C.) was used for statistical calculations.

Demographics

A total of 792 subjects participated in the study. Subject demographics were noted and somewhat different between groups (Table 2). Subjects in the methane-positive only (M+) and methane- and hydrogen-positive (H+/M+) groups were older than those in the normal (N) and hydrogen-positive only (H+) groups. The percent of females was lower in the H+ and M+ groups. Baseline GI complaints were not different between groups, although M+ subjects tended to have a greater degree of constipation than other groups (Table 2).

TABLE 2

Demographic Comparison of the Study Cohort

| Baseline | Variable | Total (n = 792) | N (n = 343) | H+ (n = 320) | M+ (n = 101) | H+/M+ (n = 28) | P Value[a] |
|---|---|---|---|---|---|---|---|
| Demographic | Age, | 47.3 ± 16.3 | 46.7 ± 16.2 | 45.7 ± 15.9 | 53.2 ± 15.5 | 50.1 ± 19.7 | <.001 |
|  | Gender, % female | 70.8 | 75.51 | 67.5 | 65.35 | 71.43 | .073 |
| Intestinal symptoms (mean VAS) | Bloating | 61.3 ± 28.4 | 61.3 ± 29.4 | 61.1 ± 27.8 | 61.7 ± 27.6 | 60.8 ± 26.2 | .97 |
|  | Abd pain | 47.9 ± 31.7 | 49.8 ± 31.4 | 46.4 ± 31.6 | 49.1 ± 32.6 | 39.0 ± 31.4 | .30 |
|  | Constipation | 42.3 ± 35.1 | 40.4 ± 34.8 | 41.8 ± 35.5 | 47.6 ± 34.8 | 52.8 ± 33.8 | .16 |
|  | Diarrhea | 35.4 ± 33.7 | 36.2 ± 33.9 | 36.0 ± 34.0 | 31.2 ± 32.9 | 34.2 ± 30.2 | .53 |

Data are expressed as mean ± SD;
[a]P value is for comparison of differences among the 4 groups.

Body Composition

Figure 15:
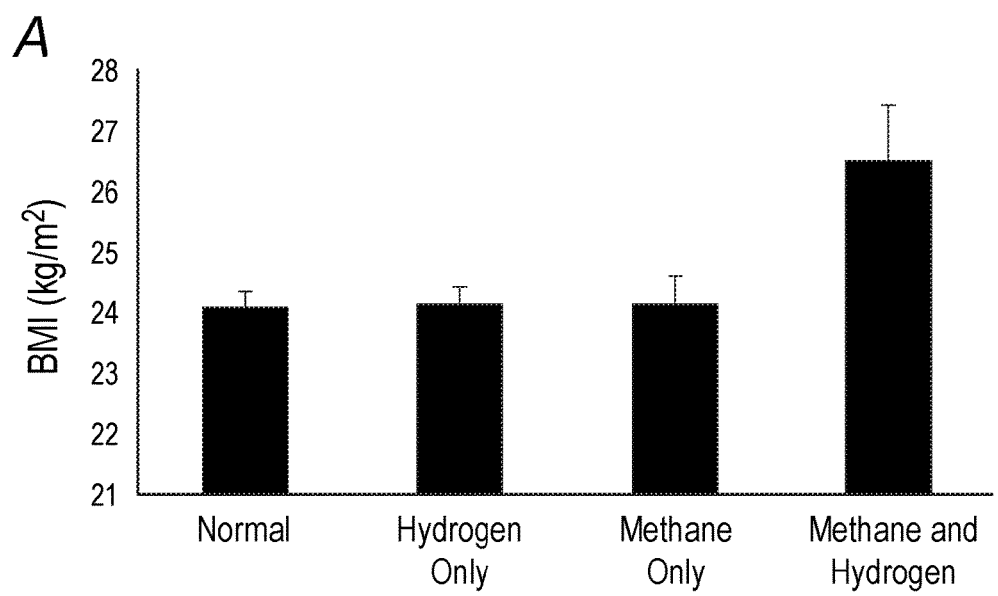
FIG. 15 depicts body composition and production of methane and hydrogen on a breath test. (A) BMI by group. A significance level of P<0.02 between the methane-and-hydrogen group and each of the other groups is shown. Error bars denote SEM. (B) Percent body fat by group. A significance level of P≤0.001 between the methane-and-hydrogen group and each of the other groups is shown.
Figure 15:
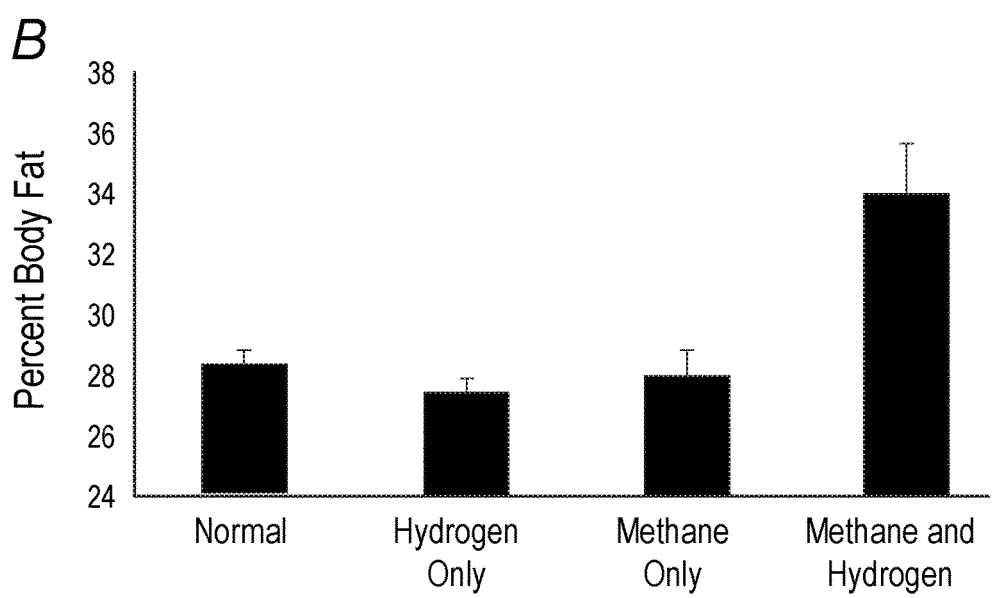

H+/M+ subjects had a greater BMI than any of the other 3 groups (FIG. 15A). Similarly, percent body fat was greatest in the H+/M+ group (FIG. 15B). Gender was not significantly different between groups. ANOVA indicated that age differed across the groups. Dunnett's post hoc test indicated that the M+ group was the only group that differed significantly from the N group for age. Adjusting for age, BMI was still significantly higher in the H+/M+ group than the other 3 groups (N: 24.1±5.2 kg/m$^2$; H+: 24.2±4.5 kg/m$^2$; M+: 24.0±3.75 kg/m$^2$; H+/M+: 26.5±7.1 kg/m2, P<0.02 for each comparison). Using a similar analysis, the H+/M+ group had a higher percent body fat than the other groups (N: 28.3±10.0%; H+: 27.5±9.0%; M+: 28.0±8.9%; H+/M+: 34.1±10.9%) (P<0.001 for each comparison).

REFERENCES

1. Ford A C, Spiegel B M, Talley N J, Moayyedi P. Small intestinal bacterial overgrowth in irritable bowel syndrome: systematic review and meta-analysis. Clin Gastroenterol Hepatol. 2009 December; 7(12):1279-86.
2. Shah E D, Basseri R J, Chong K, Pimentel M. Abnormal breath testing in IBS: a meta-analysis. Dig Dis Sci. 2010 September; 55(9):2441-9.
3. Posserud I, Stotzer P O, Björnsson E S, Abrahamsson H, Simrén M. Small intestinal bacterial overgrowth in patients with irritable bowel syndrome. Gut. 2007 June; 56(6):802-8.
4. Manolis Pyleris, Evangelos J. Giamarellos-Bourboulis, Bassileios Koussoulas, Charalambos Barbatzas, Mark Pimentel. Small Bowel Culture Confirms the Presence of Small Intestinal Bacterial Overgrowth in a Subset of IBS Subjects. Gastroenterology 2011 May; Abstract #930.
5. Pimentel M, Mayer A G, Park S, Chow E J, Hasan A, Kong Y. Methane production during lactulose breath test is associated with gastrointestinal disease presentation. Dig Dis Sci 2003; 48:86-92.
6. Attaluri A, Jackson M, Valestin J, Rao S S. Am J Gastroenterol. Methanogenic flora is associated with altered colonic transit but not stool characteristics in constipation without IBS. 2010 June; 105(6):1407-11.
7. Reddymasu S C, Sostarich S, McCallum R W. Small intestinal bacterial overgrowth in irritable bowel syndrome: are there any predictors? BMC Gastroenterol. 2010 Feb. 22; 10:23.
8. Kunkel D, Basseri R J, Makhani M D, Chong K, Chang C, Pimentel M. Methane on breath testing is associated with constipation: a systematic review and meta-analysis. Dig Dis Sci 2011; 56(6): 1612-8.
9. Chatterjee S, Park S, Low K, Kong Y, Pimentel M. The degree of breath methane production in IBS correlates with the severity of constipation. Am J Gastroenterol 2007; 102:837-841.
10. Sahakian A B, Jee S R, Pimentel M. Methane and the gastrointestinal tract. Dig Dis Sci 2010; 55:2135-2143.
11. Miller T L, Wolin M J. Enumeration of *Methanobrevibacter smithii* in human feces. Arch Microbiol 1982; 131:14-18.
12. Weaver G A, Krause J A, Miller T L, Wolin M J. Incidence of methanogenic bacteria in a sigmoidoscopy population: an association of methanogenic bacteria and diverticulosis. Gut 1986; 27:698-704.
13. Hwang L, Low K, Khoshini R, Melmed G, et al. Evaluating breath methane as a diagnostic test for constipation-predominant IBS. Dig Dis Sci 2010; 55:398-403.
14. Pimentel M, Lin H C, Enayati P, van den Burg B, et al. Methane, a gas produced by enteric bacteria, slows intestinal transit and augments small intestinal contractile activity. Am J Physiol Gastrointest Liver Physiol 2006; 290:G1089-1095.
15. Fiedorek S C, Pumphrey C L, Casteel HB. Breath methane production in children with constipation and encopresis. J Pediatr Gastroenterol Nutr 1990; 10:473-477.
16. Soares A C, Lederman H M, Fagundes-Neto U, de Morais M B. Breath methane associated with slow colonic transit time in children with chronic constipation. J Clin Gastroenterol 2005; 39:512-515.
17. Pimentel M, Chow E J, Lin H C. Normalization of lactulose breath testing correlates with symptom improvement in irritable bowel syndrome. a double-blind, randomized, placebo-controlled study. Am J Gastroenterol 2003; 98:412-419.
18. Ghoshal U C, Srivastava D, Verma A, Misra A. Slow transit constipation associated with excess methane production and its improvement following rifaximin therapy: a case report. J Neurogastroenterol Motil. 2011 April; 17(2): 185-8
19. Pimentel M, Chatterjee S, Chow E J, Park S, Kong Y. Neomycin improves constipation-predominant irritable bowel syndrome in a fashion that is dependent on the presence of methane gas: subanalysis of a double-blind randomized controlled study. Dig Dis Sci 2006; 51:1297-1301.
20. Low K, Hwang L, Hua J, Zhu A, Morales W, Pimentel M. A combination of rifaximin and neomycin is most effective in treating irritable bowel syndrome patients with methane on lactulose breath test. J Clin Gastroenterol 2010, 44(8):547-50.

REFERENCES "A"

1. Gill S R, Pop M, Deboy R T et al. Metagenomic analysis of the human distal gut microbiome. *Science* 2006; 312: 1355-1359.
2. Turnbaugh P J, Ley R E, Hamady M et al. The human microbiome project. *Nature* 2007; 449: 804-810.
3. Savage DC. Microbial ecology of the gastrointestinal tract. *Annu Rev Microbiol* 1977; 31:107-133.
4. Simon G L, Gorbach S L. Intestinal flora in health and disease. *Gastroenterology* 1984; 86:174-193.
5. Peled Y, Gilat T, Liberman E, Bujanover Y. The development of methane production in childhood and adolescence. *J Pediatr Gastroenterol Nutr* 1985; 4:575-579.
6. Bäckhed F, Ley R E, Sonnenburg J L, Peterson D A, Gordon J I. Host-bacterial mutualism in the human intestine. *Science* 2005; 307: 1915-1920.
7. Sahakian A B, Jee S R, Pimentel M. Methane and the gastrointestinal tract. *Dig Dis Sci* 2010; 55:2135-2143.
8. Bäckhed F, Manchester J K, Semenkovich C F, Gordon J I. Mechanisms underlying the resistance to diet-induced obesity in germ-free mice. *Proc Natl Acad Sci USA* 2007; 104:979-984.
9. Turnbaugh P J, Ley R E, Mahowald M A et al. An obesity-associated gut microbiome with increased capacity for energy harvest. *Nature* 2006; 444:1027-1031.
10. Cani P D, Amar J, Iglesias M A et al. Metabolic endotoxemia initiates obesity and insulin resistance. *Diabetes* 2007; 56:1761-1772.
11. Backhed F, Ding H, Wang T et al. The gut microbiota as an environmental factor that regulates fat storage. *Proc Natl Acad Sci USA* 2004; 101:15718-15723.
12. Ley R E, Turnbaugh P J, Klein S, Gordon J I. Microbial ecology: human gut microbes associated with obesity. *Nature* 2006; 444:1022-1023.
13. Cani P D, Bibiloni R, Knauf C et al. Changes in gut microbiota control metabolic endotoxemia-induced inflammation in high-fat diet-induced obesity and diabetes in mice. *Diabetes* 2008; 57:1470-1481.
14. Musso G, Gambino R, Cassader M. Interactions between gut microbiota and host metabolism predisposing to obesity and diabetes. *Annu Rev Med* 2011; 62:361-380.
15. Cani P D, Delzenne N M. The gut microbiome as therapeutic target. *Pharmacol Ther* 2011; 130:202-212.
16. Jones W J, Nagle D P Jr, Whitman W B. Methanogens and the diversity of archaebacteria. *Microbiol Rev* 1987; 51:135-177.
17. McKay L F, Holbrook W P, Eastwood M A. Methane and hydrogen production by human intestinal anaerobic bacteria. *Acta Pathol Microbiol Immunol Scand B* 1982; 90:257-260.
18. Gibson G R, Cummings J H, Macfarlane G T et al. Alternative pathways for hydrogen disposal during fermentation in the human colon. *Gut* 1990; 31:679-683.
19. Pimentel M, Mayer A G, Park S et al. Methane production during lactulose breath test is associated with gastrointestinal disease presentation. *Dig Dis Sci* 2003; 48:86-92.
20. Pimentel M, Chow E J, Lin H C. Normalization of lactulose breath testing correlates with symptom improvement in irritable bowel syndrome. A double-blind, randomized, placebo-controlled study. *Am J Gastroenterol* 2003; 98:412-419.
21. Flourié B, Etanchaud F, Florent C et al. Comparative study of hydrogen and methane production in the human colon using caecal and faecal homogenates. *Gut* 1990; 31:684-685.
22. Samuel B S, Gordon J I. A humanized gnotobiotic mouse model of host-archaeal-bacterial mutualism. *Proc Natl Acad Sci USA* 2006; 103:10011-10016.
23. Mathur R, Amichai M, Mirocha J et al. Concomitant methane and hydrogen production in humans is associated with a higher body mass index. *Gastroenterology* 2011; 140:S-335.
24. Miller T L, Wolin M J. Methanosphaera stadtmaniae gen. nov., sp. nov.: a species that forms methane by reducing methanol with hydrogen. *Arch Microbiol* 1985; 141:116-122.
25. Zhang H, DiBaise J K, Zuccolo A et al. Human gut microbiota in obesity and after gastric bypass. *Proc Natl Acad Sci USA* 2009; 106:2365-2370.
26. Nava G M, Carbonero F, Croix J A, Greenberg E, Gaskins H R. Abundance and diversity of mucosa-associated hydrogenotrophic microbes in the healthy human colon. *ISMS J* 2012; 6:57-70.
27. Pimentel M, Chatterjee S, Chang C et al. A new rat model links two contemporary theories in irritable bowel syndrome. *Dig Dis Sci* 2008; 53:982-989.
28. Hooper L V, Midtvedt T, Gordon J I. How host-microbial interactions shape the nutrient environment of the mammalian intestine. *Annu Rev Nutr* 2002; 22:283-307.
29. Ridlon J M, Kang D J, Hylemon P B. Bile salt biotransformations by human intestinal bacteria. *J Lipid Res* 2006; 47:241-259.
30. Kim J J, Sears D D. TLR4 and insulin resistance. *Gastroenterol Res Pract* 2010; 2010:212563.
31. Ley R E, Bäckhed F, Turnbaugh P et al. Obesity alters gut microbial ecology. *Proc Natl Acad Sci USA* 2005; 102:11070-11075.
32. Chen M, Wolin M J. Effect of monensin and lasalocid-sodium on the growth of methanogenic and rumen saccharolytic bacteria. *Appl Environ Microbiol* 1979; 38:72-77.
33. Freeland K R, Wilson C, Wolever T M. Adaptation of colonic fermentation and glucagon-like peptide-1 secretion with increased wheat fibre intake for 1 year in hyperinsulinaemic human subjects. *Br J Nutr* 2010; 103: 82-90.
34. Freeland K R, Wolever T M. Acute effects of intravenous and rectal acetate on glucagon-like peptide-1, peptide YY, ghrelin, adiponectin and tumour necrosis factor-alpha. *Br J Nutr* 2010; 103:460-466.
35. Chatterjee S, Park S, Low K, Kong Y, Pimentel M. The degree of breath methane production in IBS correlates with the severity of constipation. *Am J Gastroenterol* 2007; 102:837-841.
36. Fiedorek S C, Pumphrey C L, Casteel HB. Breath methane production in children with constipation and encopresis. *J Pediatr Gastroenterol Nutr* 1990; 10:473-477.
37. Peled Y, Weinberg D, Hallak A, Gilat T. Factors affecting methane production in humans. Gastrointestinal diseases and alterations of colonic flora. *Dig Dis Sci* 1987; 32:267-271.
38. Pimentel M, Lin H C, Enayati P et al. Methane, a gas produced by enteric bacteria, slows intestinal transit and augments small intestinal contractile activity. *Am J Physiol Gastrointest Liver Physiol* 2006; 290:G1089-G1095.
39. Parkman H P, Yates K, Hasler W L et al. Clinical features of idiopathic gastroparesis vary with sex, body mass, symptom onset, delay in gastric emptying, and gastroparesis severity. *Gastroenterology* 2011; 140:101-115.

40. Kunkel D, Basseri B, Low K et al. Efficacy of the glucagon-like peptide-1 agonist exenatide in the treatment of short bowel syndrome. *Neurogastroenterol Motil* 2011; 23:739-e328.

REFERENCES "B"

1. Malnick S D, Knobler H. The medical complications of obesity. *Q J M.* 2006; 99:565-579.
2. Flegal K M, Graubard B I, Williamson D F, Gail M H. Cause-specific excess deaths associated with underweight, overweight, and obesity. *JAMA.* 2007; 298:2028-2037.
3. Turnbaugh P J, Ley R E, Mahowald M A, Magrini V, Mardis E R, Gordon J I. An obesity-associated gut microbiome with increased capacity for energy harvest. *Nature.* 2006; 444:1027-1031.
4. Ley R E, Turnbaugh P J, Klein S, Gordon J I. Microbial ecology: human gut microbes associated with obesity. *Nature.* 2006; 444:1022-1023.
5. Cani P D, Bibiloni R, Knauf C, et al. Changes in gut microbiota control metabolic endotoxemia-induced inflammation in high-fat diet-induced obesity and diabetes in mice. *Diabetes.* 2008; 57:1470-1481.
6. Ley R E, Backhed F, Turnbaugh P, Lozupone C A, Knight R D, Gordon J I. Obesity alters gut microbial ecology. *Proc Natl Acad Sci USA.* 2005; 102:11070-11075.
7. Samuel B S, Gordon J I. A humanized gnotobiotic mouse model of host-archaeal-bacterial mutualism. *Proc Natl Acad Sci USA.* 2006; 103:10011-10016.
8. Schink B. Energetics of syntrophic cooperation in methanogenic degradation. *Microbiol Mol Biol Rev.* 1997; 61:262-280.
9. Flourie B, Etanchaud F, Florent C, Pellier P, Bouhnik Y, Rambaud J C. Comparative study of hydrogen and methane production in the human colon using caecal and faecal homogenates. *Gut.* 1990; 31: 684-685.
10. Kim G, Deepinder F, Morales W, et al. *Methanobrevibacter smithii* is the predominant methanogen in patients with constipation-predominant IBS and methane on breath. *Digest Dis Sci.* 2012; 57(12): 3213-3218.
11. Basseri R J, Basseri B, Pimentel M, et al. Intestinal methane production in obese individuals is associated with a higher body mass index. *Gastroenterol Hepatol.* 2012; 8:22-28.
12. Gibson A L, Holmes J C, Desautels R L, Edmonds L B, Nuudi L. Ability of new octapolar bioimpedance spectroscopy analyzers to predict 4-component-model percentage body fat in Hispanic, black, and white adults. *Am J Clin Nutr.* 2008; 87:332-338.
13. Pimentel M, Mayer A G, Park S, Chow E J, Hasan A, Kong Y. Methane production during lactulose breath test is associated with gastrointestinal disease presentation. *Digest Dis Sci.* 2003; 48:86-92.
14. Backhed F, Ding H, Wang T, et al. The gut microbiota as an environmental factor that regulates fat storage. *Proc Natl Acad Sci USA.* 2004; 101:15718-15723.
15. Backhed F, Manchester J K, Semenkovich C F, Gordon J I. Mechanisms underlying the resistance to diet-induced obesity in germ-free mice. *Proc Natl Acad Sci USA.* 2007; 104:979-984.
16. Cani P D, Lecourt E, Dewulf E M, et al. Gut microbiota fermentation of prebiotics increases satietogenic and incretin gut peptide production with consequences for appetite sensation and glucose response after a meal. *J Clin Nutr.* 2009; 90:1236-1243.
17. Samuel B S, Shaito A, Motoike T, et al. Effects of the gut microbiota on host adiposity are modulated by the short-chain fatty-acid binding G protein-coupled receptor, Gpr41. *Proc Natl Acad Sci USA.* 2008; 105:16767-16772.
18. Mathur R, Kim G, Morales W, et al. Intestinal *Methanobrevibacter smithii* but not total bacteria is related to diet-induced weight gain in rats. *Obesity* (Silver Spring)., in press.
19. Pimentel M, Lin H C, Enayati P, et al. Methane, a gas produced by enteric bacteria, slows intestinal transit and augments small intestinal contractile activity. *Am J Physiol.* 2006; 290:G1089-G1095.
20. Peled Y, Gilat T, Liberman E, Bujanover Y. The development of methane production in childhood and adolescence. *J Pediatr Gastroenterol Nutr.* 1985; 4:575-579.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method, comprising:
   subjecting a biological sample from a subject to analysis for methanogen quantity, wherein the biological sample is stool and the analysis comprises using quantitative polymerase chain reaction (qPCR);
   comparing the methanogen quantity to a reference value, wherein the reference value is about 10,000 cfu per ml of the biological sample;
   selecting a statin for the subject if the methanogen quantity is higher than the reference value based on the recognition that the statin is appropriate for subjects who have a methanogen quantity higher than the reference value; and
   administering an effective amount of the statin to the subject,
   wherein the subject is obese, and the obesity is caused by or associated with having a high methanogen quantity.

2. The method of claim 1, further comprising subjecting the biological sample to analysis for a quantity of a methanogen syntrophic microorganism.

3. The method of claim 2, wherein the methanogen syntrophic microorganism is a hydrogen-producing microorganism.

4. The method of claim 2, further comprising selecting a therapy to inhibit the growth of the methanogen syntrophic microorganism.

5. The method of claim 4, further comprising administering to the subject the therapy to inhibit the growth of the methanogen syntrophic microorganism.

6. The method of claim 1, wherein the methanogen is from the genus *Methanobrevibacter*.

7. The method of claim 6, wherein the *Methanobrevibacter* is *Methanobrevibacter smithii* (*M. Smithii*).

8. The method of claim 1, wherein the statin is selected from the group consisting of atorvastatin, fluvastatin, lovastatin, pitavastatin, pravastatin, rosuvastatin, simvastatin, and combinations thereof.

9. The method of claim 8, wherein the statin is lovastatin.

10. The method of claim 1, further comprising administering an anti-obesity drug to the subject.

11. The method of claim 10, wherein the anti-obesity drug is selected from the group consisting of phentermine, phentermine/topiramate, xenical, lorcaserin, and rimonabant.

12. A method, comprising:
    subjecting a biological sample from a subject to analysis for methanogen quantity, wherein the biological sample is stool and the analysis comprises using quantitative polymerase chain reaction (qPCR);
    comparing the methanogen quantity to a reference value, wherein the reference value is less than 10,000 cfu per ml of the biological sample and more than about 500 cfu per ml of the biological sample;

selecting a statin for the subject if the methanogen quantity is within the reference values based on the recognition that the statin is appropriate for subjects who have a methanogen quantity higher than the reference value; and administering an effective amount of the statin to the subject, wherein the subject is obese, and the obesity is caused by or associated with having a high methanogen quantity.

13. The method of claim 12, wherein the statin is selected from the group consisting of atorvastatin, fluvastatin, lovastatin, pitavastatin, pravastatin, rosuvastatin, simvastatin, and combinations thereof.

14. The method of claim 13, wherein the reference value is less than about 9,000 cfu per ml of the biological sample.

15. The method of claim 13, wherein the reference value is less than about 8,000 cfu per ml of the biological sample.

16. The method of claim 13, wherein the reference value is less than about 7,000 cfu per ml of the biological sample.

17. The method of claim 13, wherein the reference value is less than about 6,000 cfu per ml of the biological sample.

18. The method of claim 13, wherein the reference value is less than about 5,000 cfu per ml of the biological sample.

19. The method of claim 13, wherein the reference value is less than about 4,000 cfu per ml of the biological sample.

20. The method of claim 13, wherein the reference value is less than about 3,000 cfu per ml of the biological sample.

21. The method of claim 13, wherein the reference value is less than about 2,000 cfu per ml of the biological sample.

22. The method of claim 13, wherein the reference value is less than about 1,000 cfu per ml of the biological sample.

23. The method of claim 13, wherein the reference value is about 500 cfu per ml of the biological sample.

* * * * *